(12) United States Patent
Matityahu et al.

(10) Patent No.: US 8,906,023 B2
(45) Date of Patent: Dec. 9, 2014

(54) INTRAMEDULLARY ROD FOR PIVOTING A FASTENER

(75) Inventors: Amir M. Matityahu, Los Altos, CA (US); Robert Trigg McClellan, San Francisco, CA (US)

(73) Assignee: Epix Orthopaedics, Inc., Los Altos, CA (US)

(*) Notice: Subject to any disclaimer, the term of this patent is extended or adjusted under 35 U.S.C. 154(b) by 883 days.

(21) Appl. No.: 12/143,798

(22) Filed: Jun. 22, 2008

(65) Prior Publication Data

US 2009/0048600 A1 Feb. 19, 2009

Related U.S. Application Data

(60) Provisional application No. 60/936,887, filed on Jun. 22, 2007.

(51) Int. Cl.
*A61B 17/76* (2006.01)
*A61B 17/74* (2006.01)
*A61B 17/72* (2006.01)

(52) U.S. Cl.
CPC .............. *A61B 17/744* (2013.01); *A61B 17/748* (2013.01); *A61B 17/7241* (2013.01); *A61B 17/725* (2013.01)
USPC .......................................................... 606/64

(58) Field of Classification Search
CPC ............................ A61B 17/72; A61B 17/7241
USPC .................................................. 606/60–68
See application file for complete search history.

(56) References Cited

U.S. PATENT DOCUMENTS

| | | |
|---|---|---|
| 3,783,860 A | 1/1974 | Burstein et al. |
| 4,519,100 A | 5/1985 | Wills et al. |
| 4,622,959 A | 11/1986 | Marcus |
| 4,653,487 A | 3/1987 | Maale |
| 4,657,001 A | 4/1987 | Fixel |
| 4,733,654 A | 3/1988 | Marino |
| 4,776,330 A | 10/1988 | Chapman et al. |
| 4,827,917 A | 5/1989 | Brumfield |
| 4,846,162 A | 7/1989 | Moehring |

(Continued)

FOREIGN PATENT DOCUMENTS

| | | |
|---|---|---|
| EP | 0 696 441 A2 | 2/1996 |
| EP | 0 845 245 A2 | 6/1998 |

(Continued)

OTHER PUBLICATIONS

DuPuy Orthopaedics, Inc., *Surgical Techique Femoral Troch Entry Nailing System Options Made Easy, Versanail Femoral Troth Entry*, Brochure, DePuy, a Johnson-Johnson Company, (2006) pp. 1-20.

(Continued)

*Primary Examiner* — Ellen C Hammond
(74) *Attorney, Agent, or Firm* — Intellectual Innovations Legal Advisors

(57) ABSTRACT

An intramedullary rod for use with a fastener to repair a femur includes an elongate nail extending along a longitudinal axis and having a stem and a head. The head is provided with an aperture extending along an axis at an angle to the longitudinal axis for receiving the fastener. A mechanism is carried by the head for pivoting the axis of the aperture from a first angled position relative to the head to a second angled position relative to the head. A method for using the rod and fastener is provided.

26 Claims, 23 Drawing Sheets

(56) References Cited

U.S. PATENT DOCUMENTS

| | | | |
|---|---|---|---|
| 4,881,535 A | 11/1989 | Sohngen | |
| 5,032,125 A * | 7/1991 | Durham et al. | 606/62 |
| 5,041,114 A | 8/1991 | Chapman et al. | |
| 5,047,034 A | 9/1991 | Sohngen | |
| 5,127,913 A | 7/1992 | Thomas, Jr. | |
| 5,167,663 A * | 12/1992 | Brumfield | 606/64 |
| 5,176,681 A | 1/1993 | Lawes et al. | |
| 5,190,544 A | 3/1993 | Chapman et al. | |
| 5,248,313 A | 9/1993 | Greene et al. | |
| 5,429,640 A | 7/1995 | Shuler et al. | |
| 5,454,813 A | 10/1995 | Lawes | |
| 5,514,137 A | 5/1996 | Coutts | |
| 5,545,813 A | 8/1996 | Piper | |
| 5,562,667 A | 10/1996 | Shuler et al. | |
| 5,772,662 A | 6/1998 | Chapman et al. | |
| 5,935,127 A | 8/1999 | Border | |
| 6,120,504 A | 9/2000 | Brumback et al. | |
| 6,123,708 A | 9/2000 | Kilpela et al. | |
| 6,126,661 A | 10/2000 | Faccioli et al. | |
| 6,221,074 B1 | 4/2001 | Cole | |
| 6,235,031 B1 | 5/2001 | Hodgeman et al. | |
| 6,402,753 B1 * | 6/2002 | Cole et al. | 606/62 |
| 6,406,477 B1 | 6/2002 | Fujiwara | |
| 6,443,954 B1 | 9/2002 | Bramlet et al. | |
| 6,488,684 B2 | 12/2002 | Bramlet et al. | |
| 6,562,042 B2 | 5/2003 | Nelson | |
| 6,648,889 B2 | 11/2003 | Bramlet et al. | |
| 6,702,816 B2 | 3/2004 | Buhler | |
| 6,783,529 B2 | 8/2004 | Hover et al. | |
| 6,860,691 B2 | 3/2005 | Unsworth et al. | |
| 6,893,443 B2 * | 5/2005 | Frigg et al. | 606/264 |
| 6,926,719 B2 | 8/2005 | Sohngen et al. | |
| 7,001,386 B2 * | 2/2006 | Sohngen et al. | 606/62 |
| 7,008,425 B2 | 3/2006 | Phillips | |
| 7,041,104 B1 * | 5/2006 | Cole et al. | 606/62 |
| 7,267,678 B2 | 9/2007 | Medoff | |
| 7,601,153 B2 | 10/2009 | Shinjo et al. | |
| 7,670,340 B2 | 3/2010 | Brivio et al. | |
| 7,771,428 B2 | 8/2010 | Siravo et al. | |
| 8,100,911 B2 | 1/2012 | Yamazaki et al. | |
| 2002/0133156 A1 * | 9/2002 | Cole | 606/62 |
| 2002/0151898 A1 | 10/2002 | Sohngen et al. | |
| 2002/0156473 A1 * | 10/2002 | Bramlet et al. | 606/62 |
| 2003/0036758 A1 | 2/2003 | Frigg et al. | |
| 2003/0114855 A1 * | 6/2003 | Wahl et al. | 606/67 |
| 2004/0106922 A1 | 6/2004 | Snyder | |
| 2005/0010226 A1 | 1/2005 | Grady, Jr. et al. | |
| 2005/0055023 A1 | 3/2005 | Sohngen et al. | |
| 2005/0085812 A1 | 4/2005 | Sherman et al. | |
| 2005/0149025 A1 | 7/2005 | Ferrante et al. | |
| 2005/0182405 A1 | 8/2005 | Orbay et al. | |
| 2005/0182406 A1 | 8/2005 | Orbay et al. | |
| 2005/0234457 A1 | 10/2005 | James et al. | |
| 2006/0015101 A1 | 1/2006 | Warburton et al. | |
| 2006/0058887 A1 | 3/2006 | DeSmet et al. | |
| 2006/0069392 A1 * | 3/2006 | Renzi Brivio et al. | 606/64 |
| 2006/0106398 A1 | 5/2006 | Lauryssen et al. | |
| 2006/0122600 A1 * | 6/2006 | Cole | 606/62 |
| 2007/0049938 A1 | 3/2007 | Wallace et al. | |
| 2007/0049939 A1 | 3/2007 | Wallace et al. | |
| 2007/0049940 A1 | 3/2007 | Wallace et al. | |
| 2007/0100343 A1 * | 5/2007 | Cole et al. | 606/67 |
| 2007/0123876 A1 | 5/2007 | Czartoski et al. | |
| 2007/0123878 A1 * | 5/2007 | Shaver et al. | 606/64 |
| 2007/0162016 A1 | 7/2007 | Matityahu | |
| 2007/0179835 A1 | 8/2007 | Ott, IV et al. | |
| 2007/0233100 A1 * | 10/2007 | Metzinger | 606/62 |
| 2007/0233101 A1 * | 10/2007 | Metzinger | 606/62 |
| 2007/0233102 A1 * | 10/2007 | Metzinger | 606/62 |
| 2007/0233103 A1 * | 10/2007 | Metzinger | 606/62 |
| 2007/0233104 A1 * | 10/2007 | Metzinger | 606/62 |
| 2007/0270845 A1 | 11/2007 | Watanabe et al. | |
| 2007/0270846 A1 * | 11/2007 | Metzinger | 606/64 |
| 2007/0276385 A1 | 11/2007 | Schlienger et al. | |
| 2008/0039845 A1 | 2/2008 | Bonutti et al. | |
| 2008/0091203 A1 | 4/2008 | Warburton et al. | |
| 2008/0140077 A1 * | 6/2008 | Kebaish | 606/64 |
| 2008/0147066 A1 | 6/2008 | Longsworth et al. | |
| 2008/0147067 A1 | 6/2008 | Phillips | |
| 2008/0161805 A1 | 7/2008 | Saravia et al. | |
| 2008/0287949 A1 * | 11/2008 | Keith et al. | 606/62 |
| 2009/0048598 A1 * | 2/2009 | Ritchey et al. | 606/57 |
| 2009/0048600 A1 | 2/2009 | Matityahu et al. | |
| 2009/0306666 A1 | 12/2009 | Czartoski et al. | |
| 2010/0094293 A1 | 4/2010 | McClellan et al. | |
| 2010/0268229 A1 | 10/2010 | Siravo et al. | |
| 2011/0295255 A1 | 12/2011 | Roberts et al. | |

FOREIGN PATENT DOCUMENTS

| | | |
|---|---|---|
| EP | 1 356 777 A2 | 10/2003 |
| EP | 1 557 131 A1 | 7/2005 |
| EP | 1 639 953 A1 | 3/2006 |
| GB | 2 387 112 A | 10/2003 |
| JP | 2005-270503 | 10/2005 |
| JP | 2007143942 A | 6/2007 |
| WO | WO 2003/053265 A1 | 7/2003 |
| WO | WO 2004/096067 A2 | 11/2004 |
| WO | 2005/092219 | 10/2005 |
| WO | 2005/094707 | 10/2005 |
| WO | WO 2006/066440 A2 | 6/2006 |
| WO | WO 2008/089096 A2 | 7/2008 |

OTHER PUBLICATIONS

Stryker Product, *Gamma3—The Compact Version of the Gamma Nail System—Operative Technique; Hip Fracture System Trochanteric and Long Nails*, Brochure, Literature No. LG3-OT Rev. 1, 10M 10/04, Stryker (2004) pp. 1-44 www.stryker.com.

Dec. 8, 2011 Official Action issued by the U.S. Patent Office for corresponding U.S. Appl. No. 12/576,210, pp. 1-18.

Jun. 8, 2012 Filed Response to Dec. 8, 2011 Official Action issued by the U.S. Patent Office for corresponding U.S. Appl. No. 12/576,210, pp. 1-14.

Jul. 19, 2012 Final Official Action issued by the U.S. Patent Office issued by the United States Patent Office for corresponding U.S. Appl. No. 12/576,210, pp. 1-13.

Oct. 24, 2012 Filed Response to Jul. 19, 2012 Final Official Action issued by the U.S. Patent Office for corresponding U.S. Appl. No. 12/576,210, pp. 1-10.

Translation of Mar. 3, 2011 Official Action issued by the Chinese Patent Office for corresponding CN patent application No. 200880025286.1, pp. 1-10.

Jun. 6, 2011 1st Instructional letter in response to Mar. 3, 2011 Official Action for corresponding CN patent application No. 200880025286.1, pp. 1-5.

Jul. 5, 2011 2nd Instructional letter in response to Mar. 3, 2011 Official Action for corresponding CN patent application No. 200880025286.1, pp. 1-5.

Oct. 8, 2008 International Search Report issued by the International Bureau of WIPO for corresponding PCT patent application serial No. PCT/2008/067818, p. 1.

Dec. 22, 2009 International Preliminary Report on Patentability issued by the International Bureau of WIPO Office for corresponding patent application serial No. PCT/US2008/067818, pp. 1-5.

Dec. 17, 2009 International Search Report issued by the International Bureau of WIPO for corresponding PCT patent application serial No. PCT/2009/060067, p. 1.

Apr. 12, 2011 International Preliminary Report on Patentability issued by the International Bureau of WIPO Office for corresponding patent application serial No. PCT/US2009/060067, pp. 1-5.

Extended European Search Report issued by the European Patent Office for Serial No. 08780913.3, Jun. 21, 2013, 1-5.

Advisory Action and Response after Final mailed Nov. 14, 2012 for U.S. Appl. No. 12/576,210, filed Oct. 8, 2009, pp. 1-3.

Applicant-Initiated Interview Summary mailed Feb. 25, 2014 for U.S. Appl. No. 12/576,210, filed Oct. 8, 2009, pp. 1-3.

First Patent Examination Report issued by the Australian Patent Office for Australian Patent Application Serial No. 2008268507, Dec. 4, 2012, pp. 1-4.

(56) References Cited

OTHER PUBLICATIONS

Non-Final Office Action mailed Oct. 23, 2013 for U.S. Appl. No. 12/576,210, filed Oct. 8, 2009, pp. 1-17.
Notice of Allowance and Examiner-Initiated Interview Summary mailed Mar. 26, 2014 for U.S. Appl. No. 12/576,210, filed Oct. 8, 2009, pp. 1-12.
Response mailed Feb. 21, 2014 for Non-Final Office Action dated Oct. 23, 2013 for U.S. Appl. No. 12/576,210, filed Oct. 8, 2009, pp. 1-10.
Response mailed on Jan. 3, 2014 for European office actions dated Jul. 9, 2013 and Jun. 21, 2013 for Application No. EP08780913.3 filed Jun. 22, 2008, pp. 1-9.
Response mailed Apr. 30, 2014 for Examination Report dated Dec. 4, 2012 for Australian Patent Application No. 2008268507 filed Jun. 22, 2006, pp. 1-27.
Translation of Dec. 6, 2012 Office Action issued by Japanese Patent Office for corresponding Japanese patent application No. 2010513479 filed Jun. 22, 2008, pp. 1-3.
Translation of Sep. 14, 2013 Office Action issued by Japanese Patent Office for corresponding Japanese patent application No. 2010513479 filed Jun. 22, 2008, pp. 1.
Translation of Feb. 20, 2014 Office Action issued by Japanese Patent Office for corresponding Japanese patent application No. 2010513479 filed Jun. 22, 2008, pp. 1.
Written Opinion for Application No. PCT/US2008/067818, mailed on Oct. 8, 2008, pp. 1-4.
Written Opinion for Application No. PCT/US2009/060067, mailed on Dec. 17, 2009, pp. 1-5.

* cited by examiner

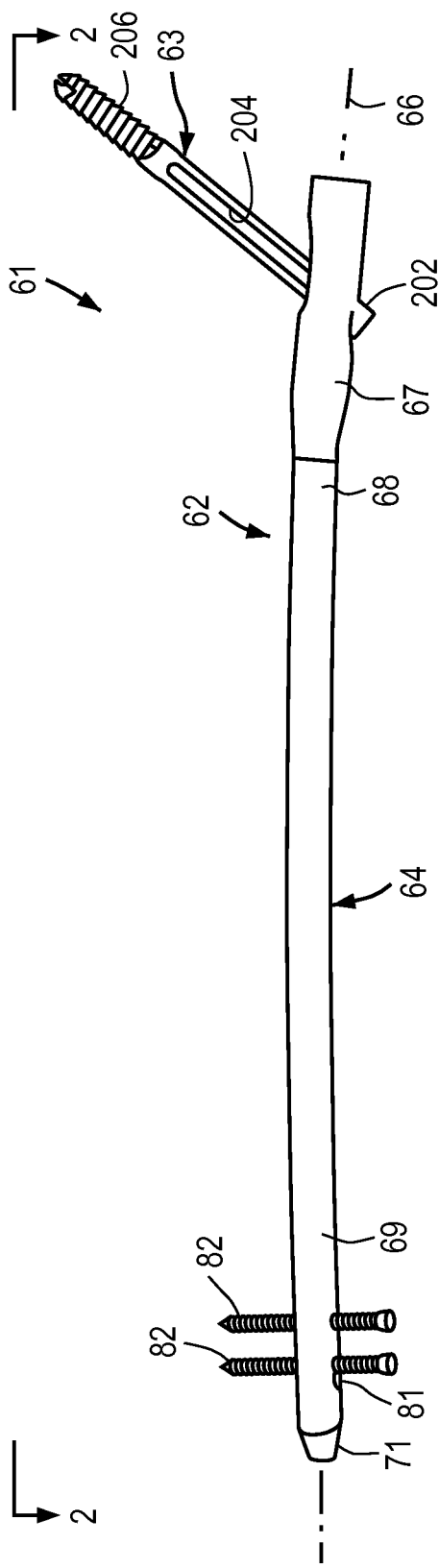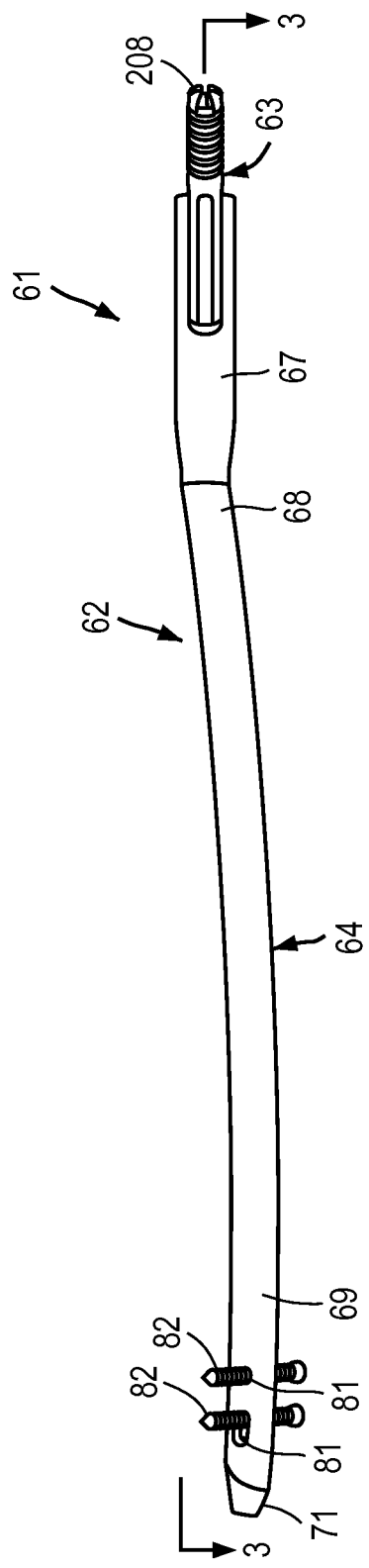

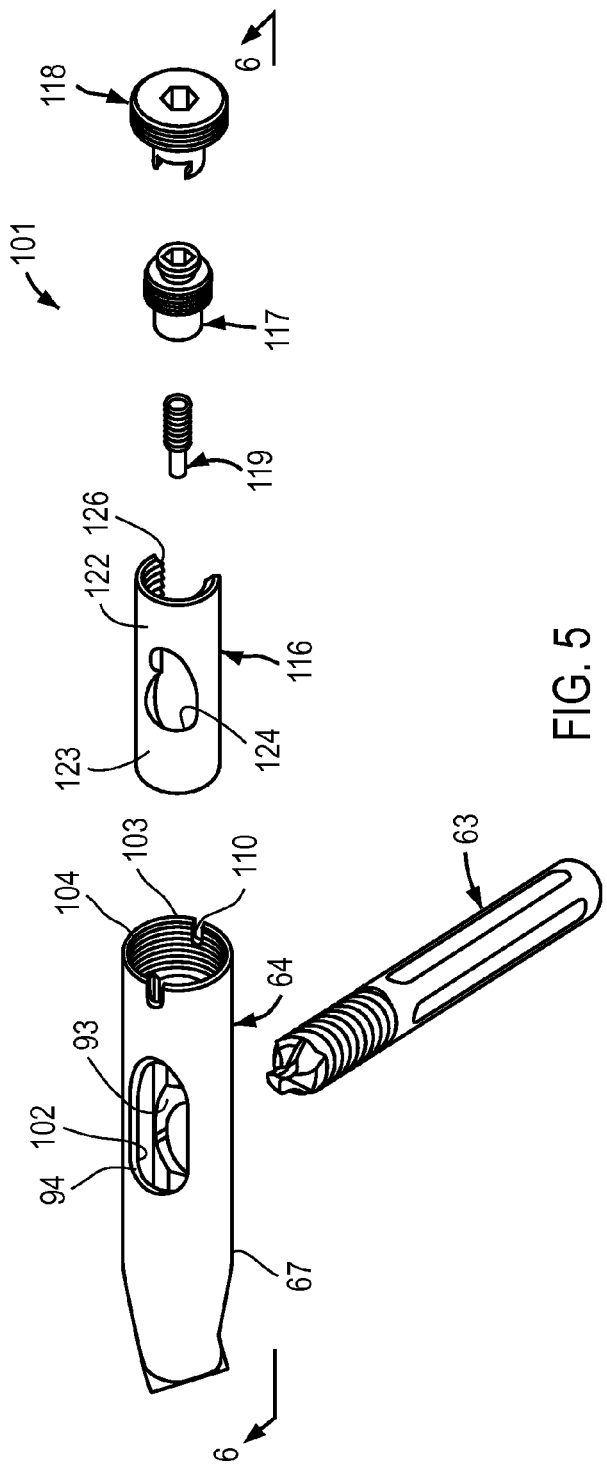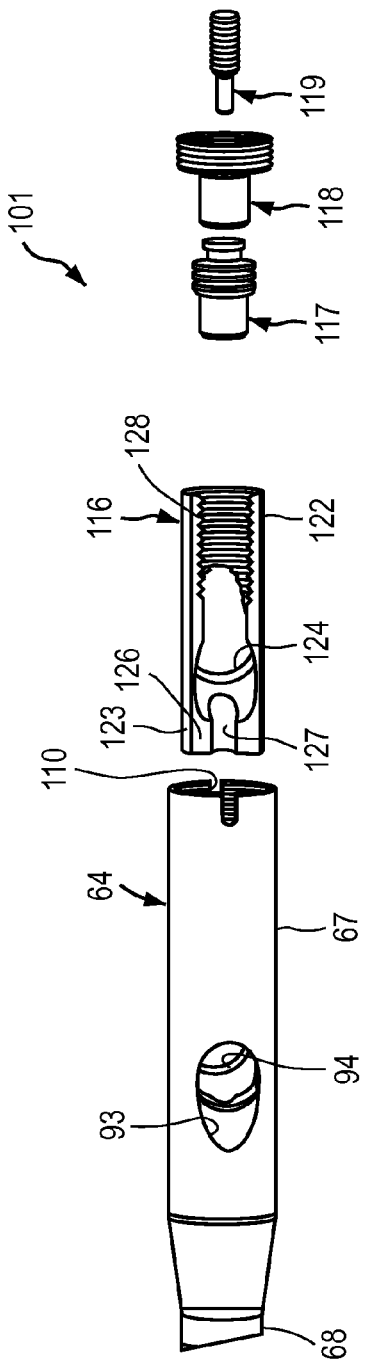

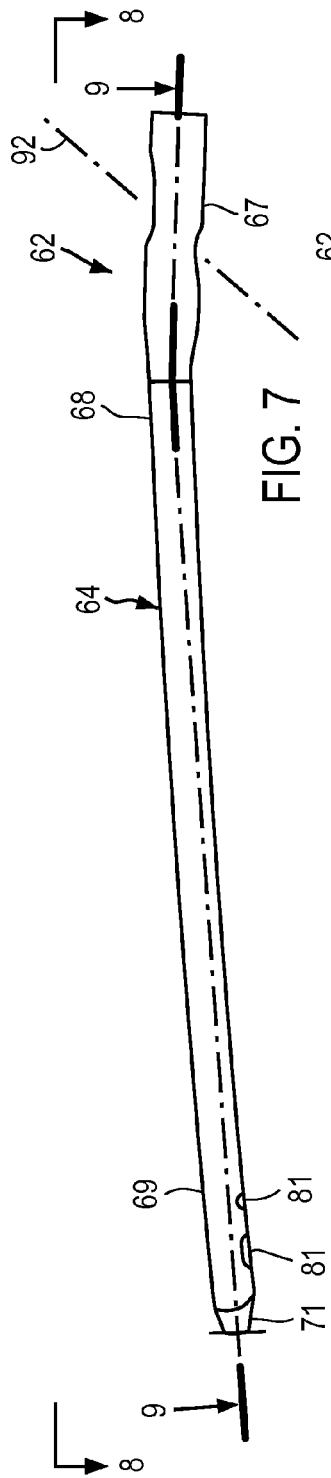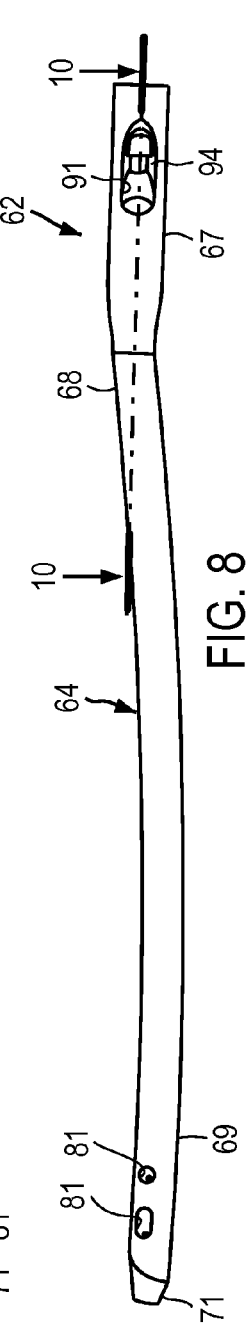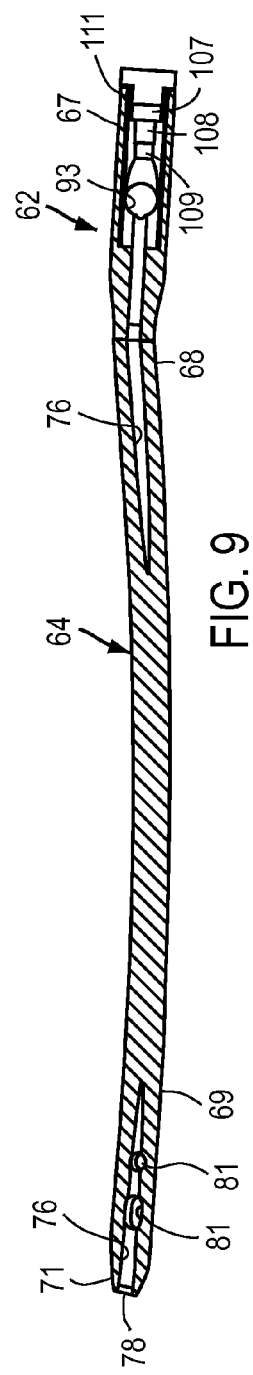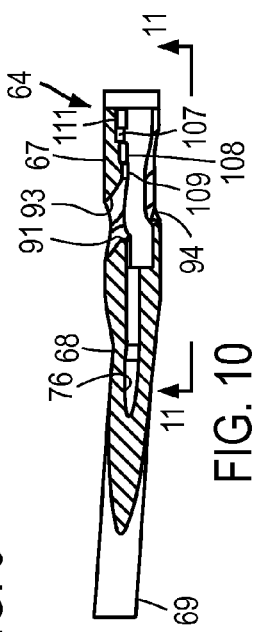

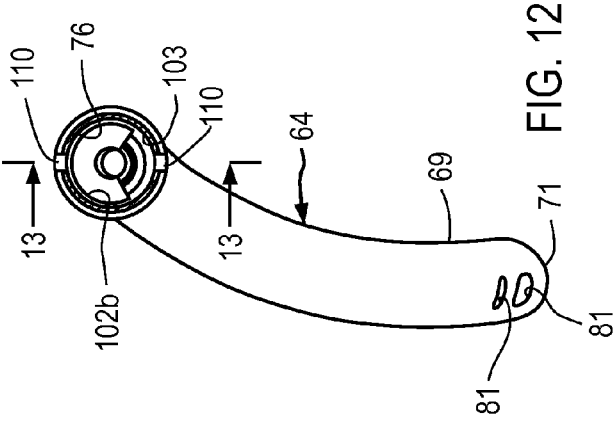
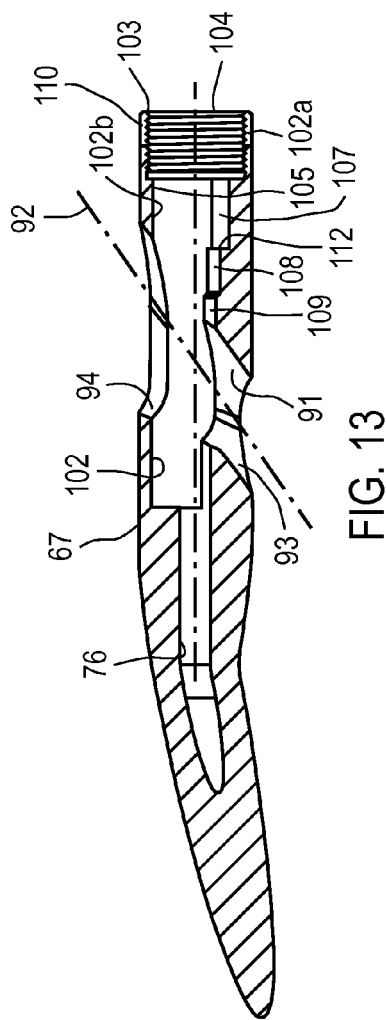
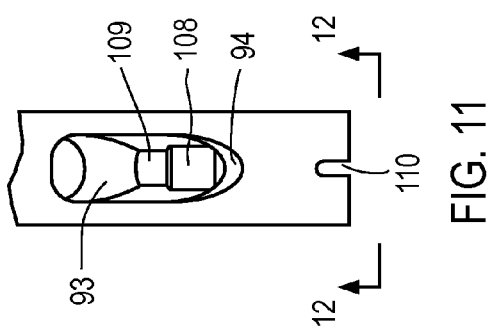

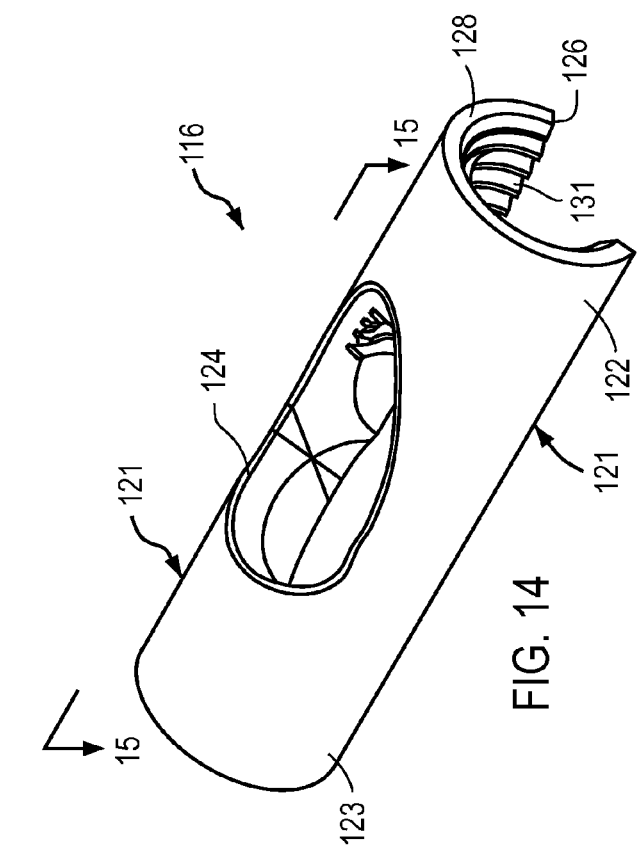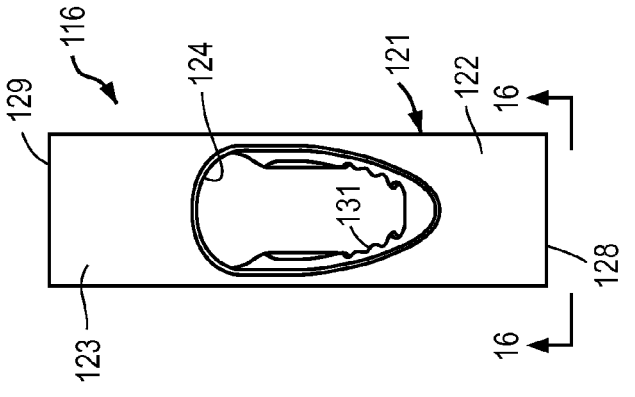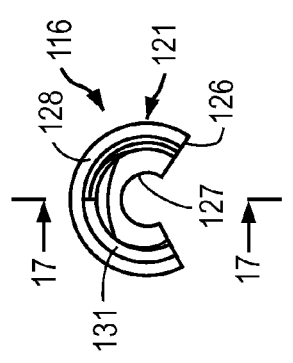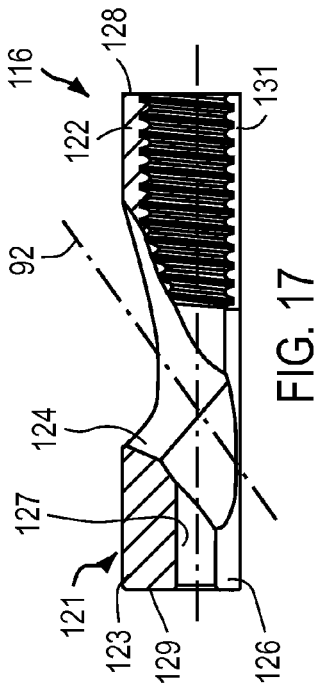

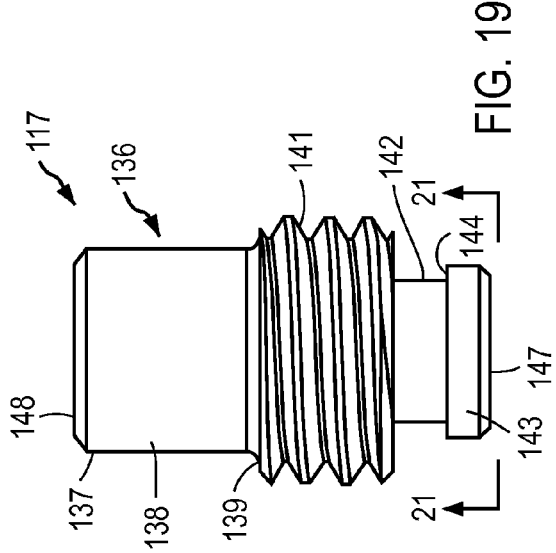
FIG. 19
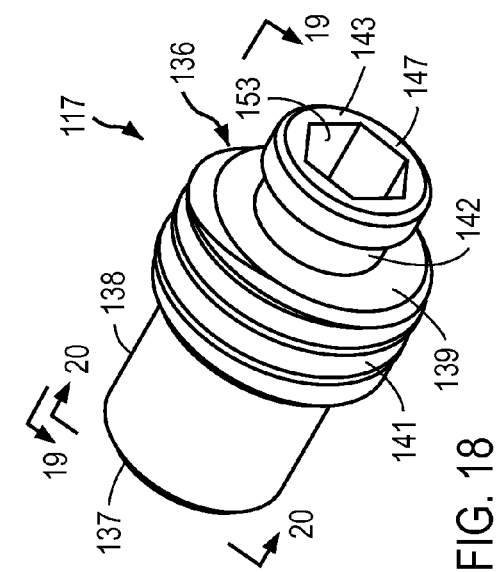
FIG. 18
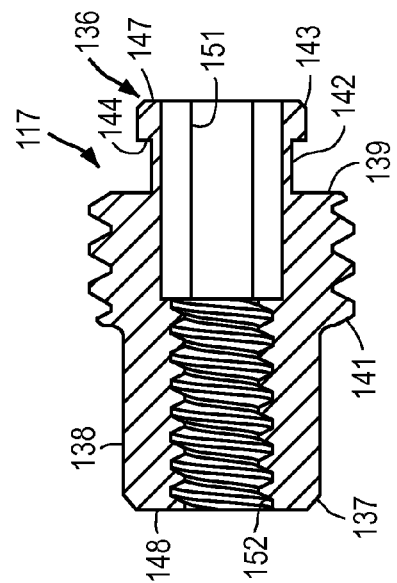
FIG. 22
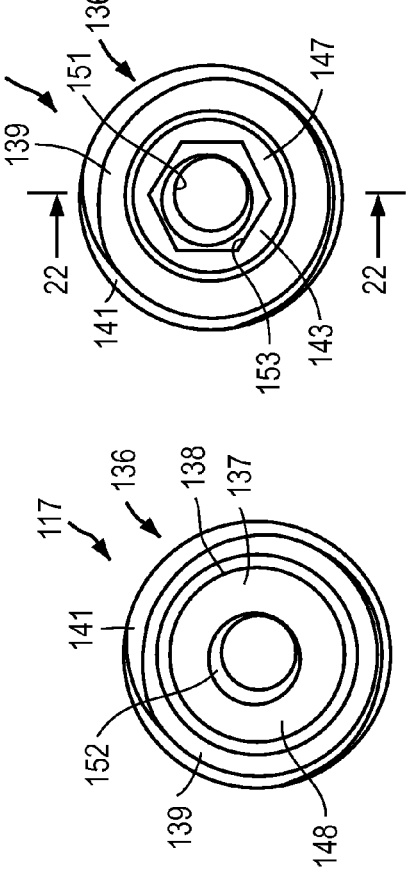
FIG. 21
FIG. 20

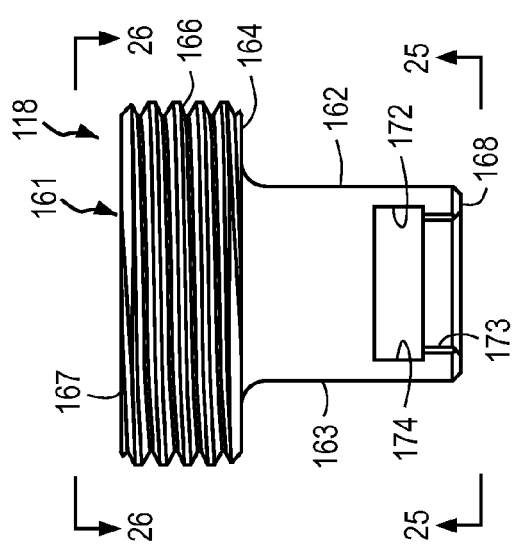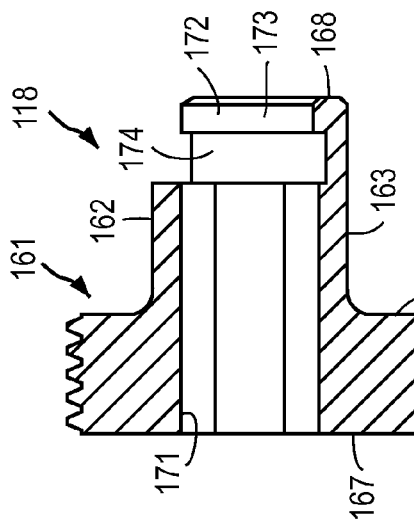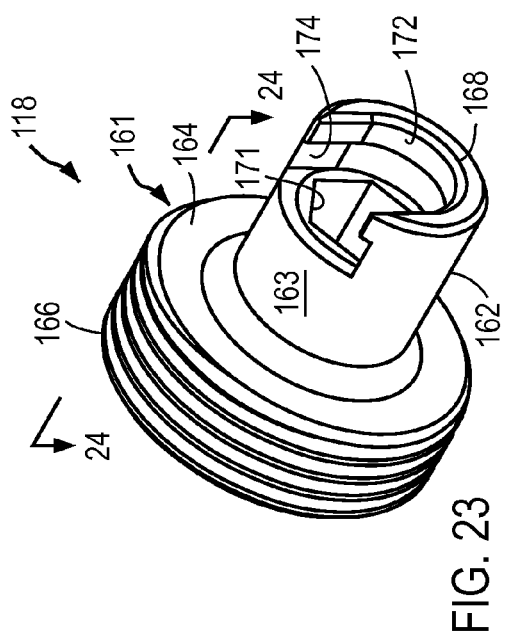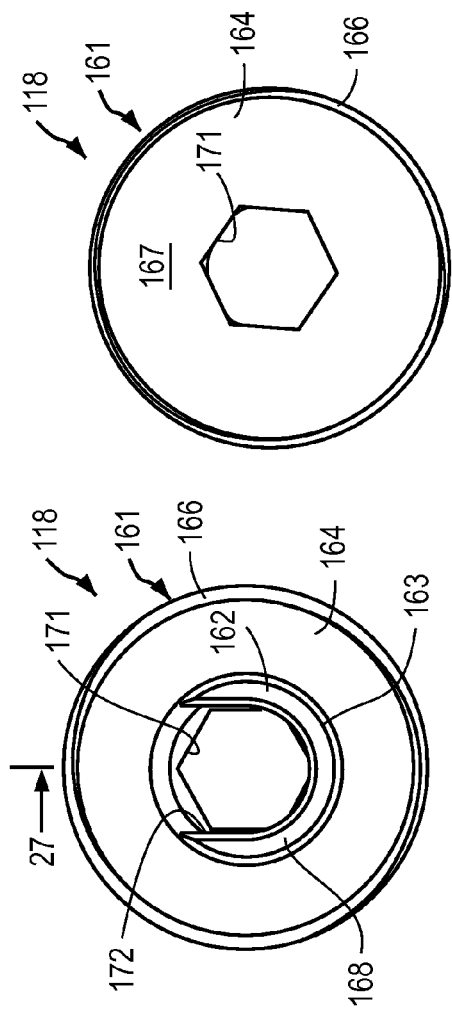

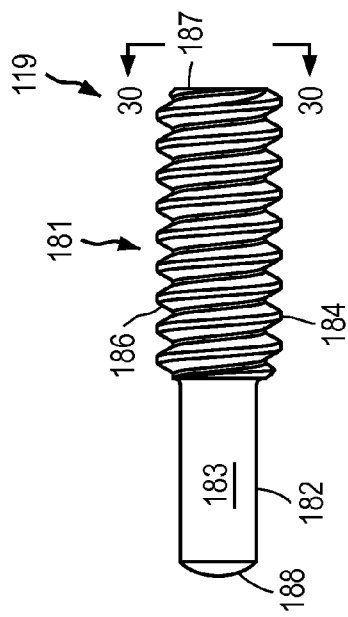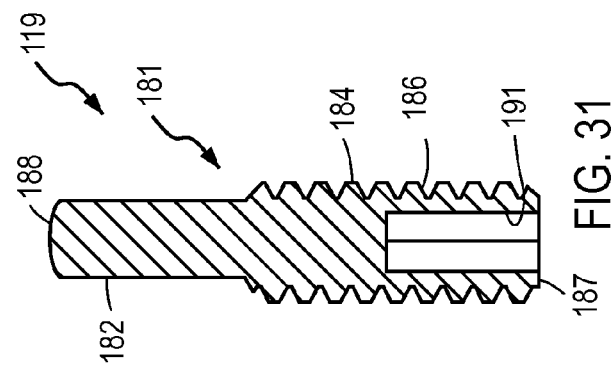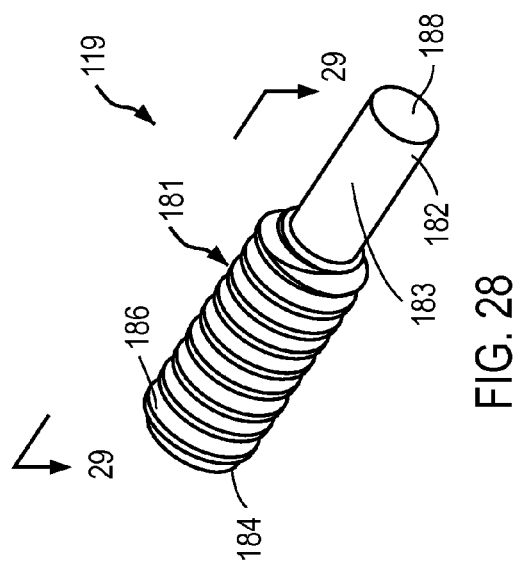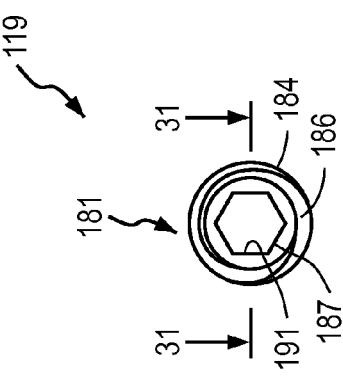

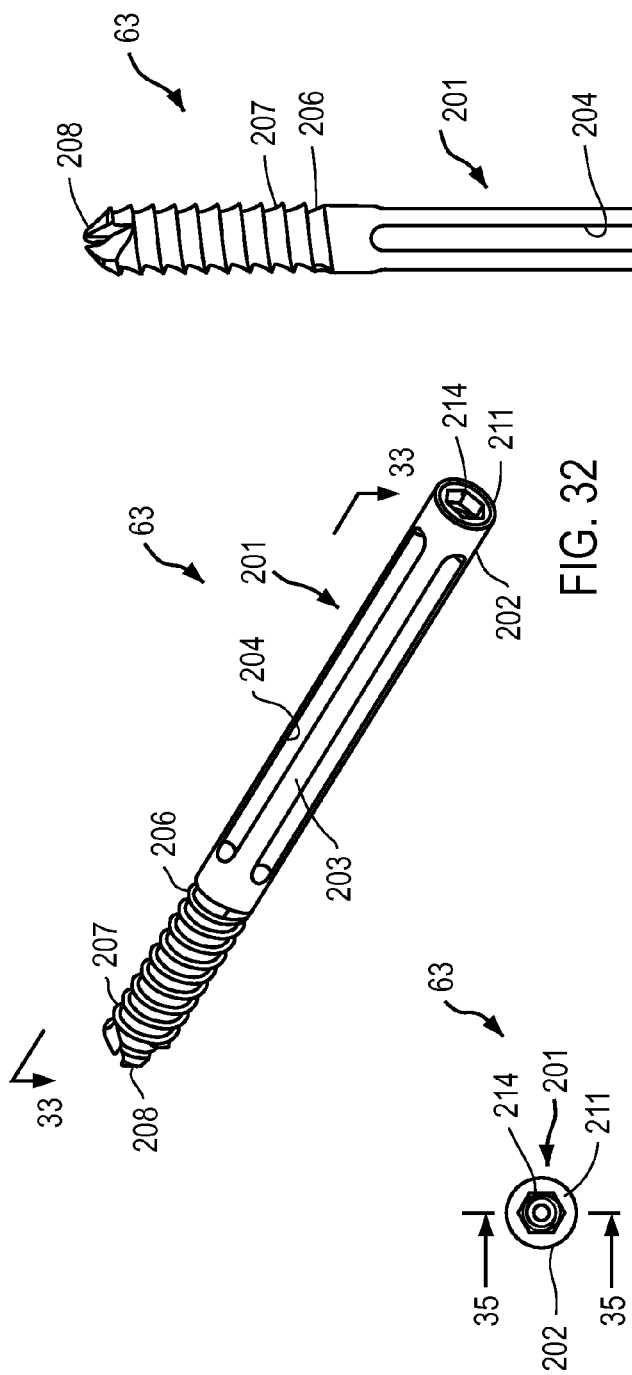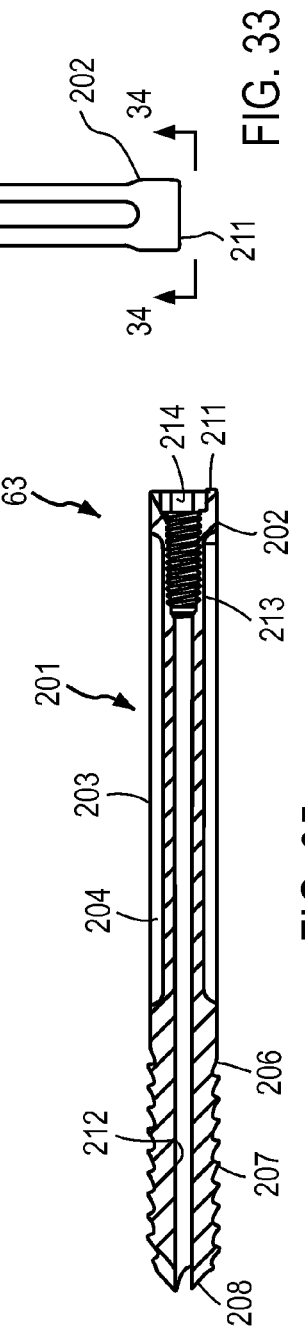

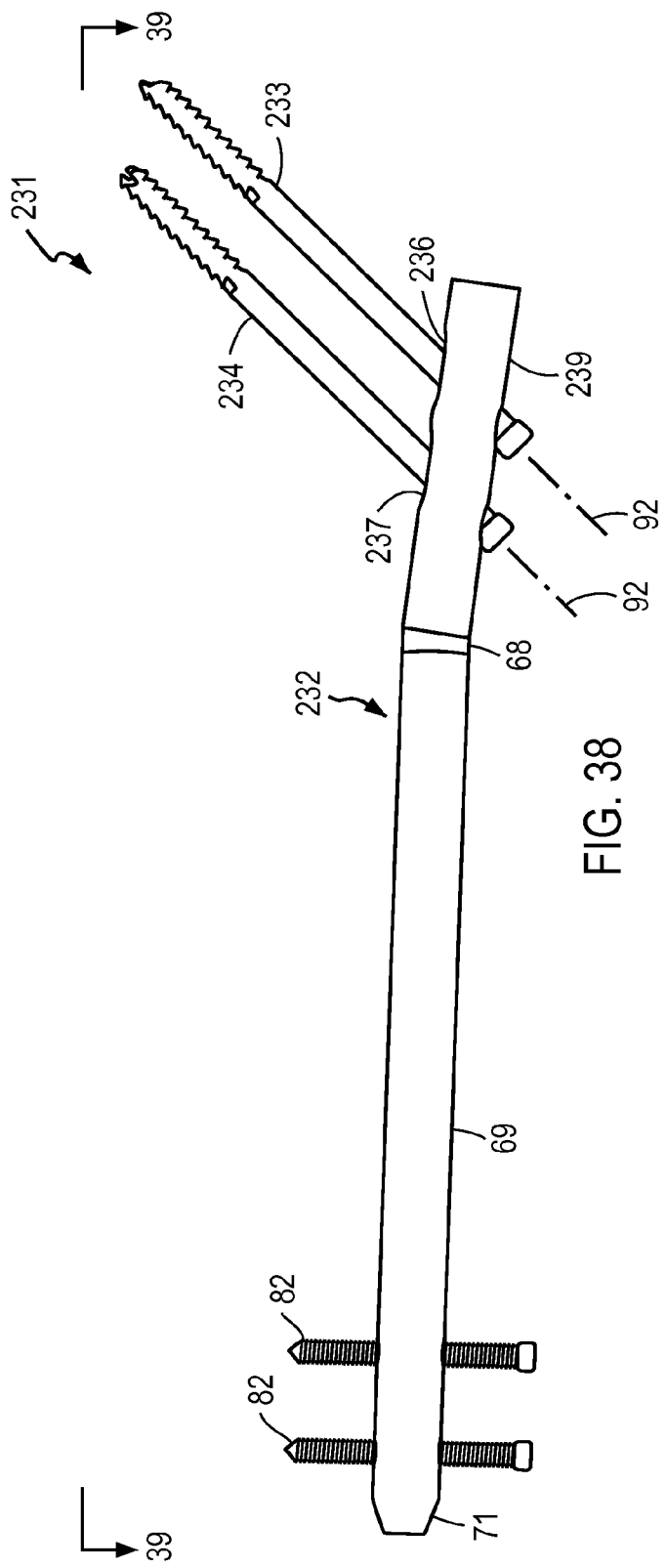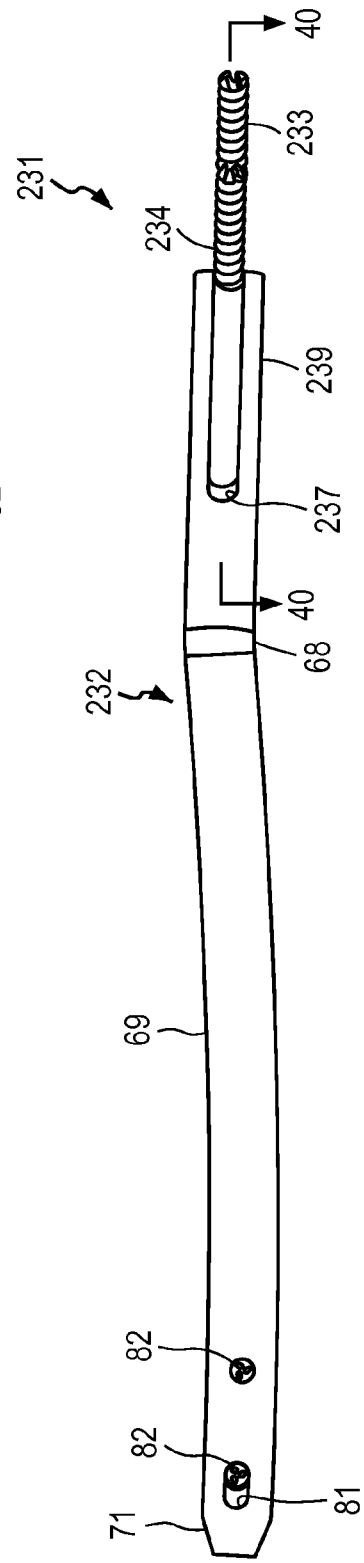

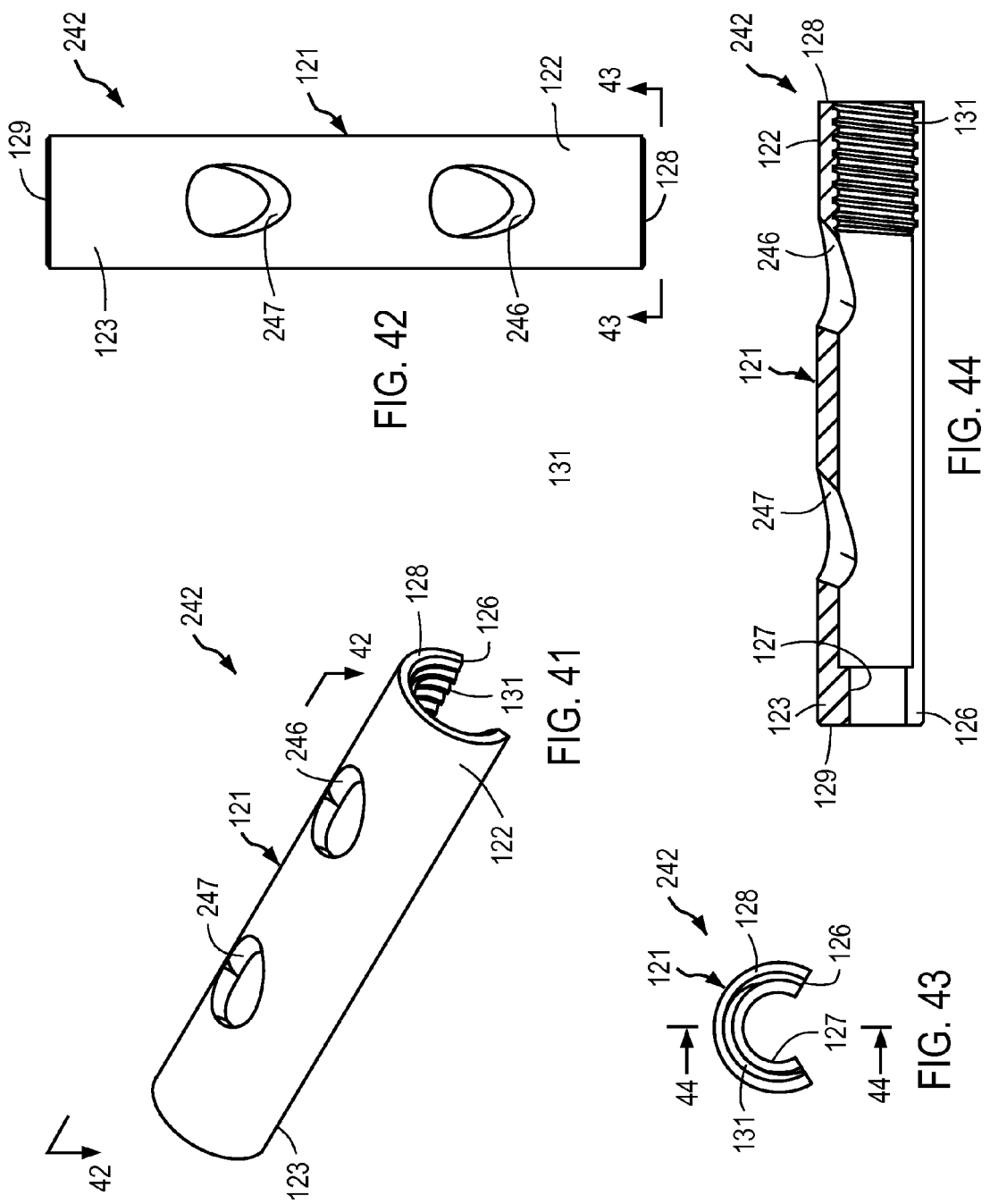

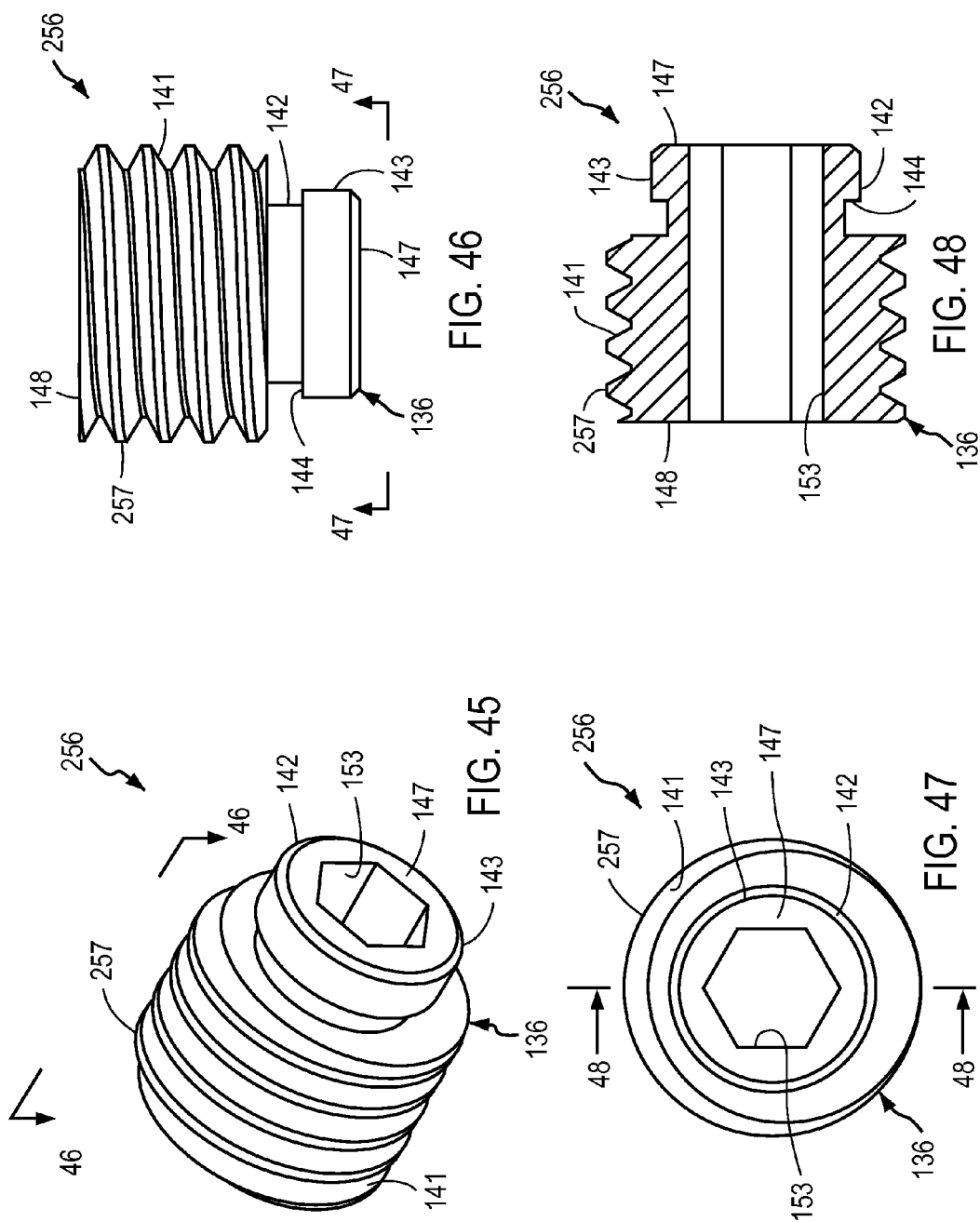

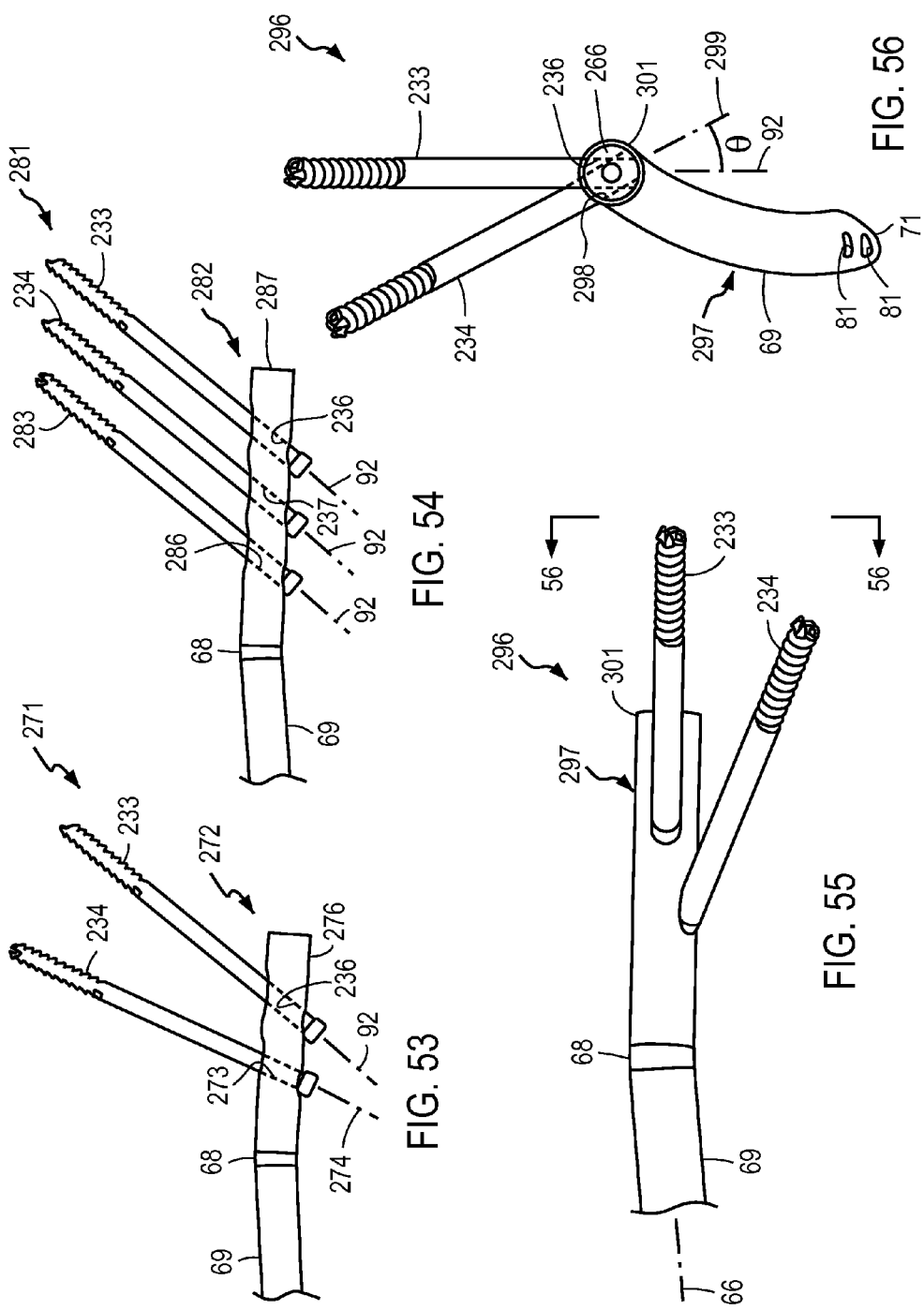

INTRAMEDULLARY ROD FOR PIVOTING A FASTENER

CROSS REFERENCE TO RELATED APPLICATION

This application claims priority to U.S. provisional patent application Ser. No. 60/936,887 filed Jun. 22, 2007, the entire content of which is incorporated herein by this reference.

FIELD OF THE INVENTION

The present invention relates to apparatus for treating bones and, more particularly, to an intramedullary rod for treating femoral fractures.

BACKGROUND OF THE INVENTION

There are a variety of devices used to treat femoral fractures. Peritrochanteric fractures of the femur have been treated with femoral rod assemblies that for example are inserted into the femoral canal to coapt the femur fractured parts. One or two angled cross-nails or locking screws are inserted through the femur and the proximal end of the intramedullary rod.

Currently available nails have been provided with static angled screws that transverse the femoral nail and then achieve adequate fixation strength in the head of the femur. They may also have slots in the nail that allow for dynamic controlled or uncontrolled compression of the fracture site in fractures of the subtrochanteric region and below, either with or without an over sleeve. Frequently, devices that treat femoral neck, intertrochanteric, and subtrochanteric fractures have varying static angles that necessitate an increased inventory to accommodate for varied static angles of the nail.

SUMMARY OF THE INVENTION

An intramedullary rod for use with a fastener to repair a femur is provided and includes an elongate nail extending along a longitudinal axis and having a stem and a head. The head is provided with an aperture extending along an axis at an angle to the longitudinal axis for receiving the fastener. A mechanism is carried by the head for pivoting the axis of the aperture from a first angled position relative to the head to a second angled position relative to the head. A method for using the rod and fastener is provided.

BRIEF DESCRIPTION OF THE DRAWINGS

The drawings described herein are for illustration purposes only and are not intended to limit the scope of the present disclosure in any way.

FIG. 1 is a front view of one embodiment of an intramedullary rod with pivotable fastener of the present invention.

FIG. 2 is a side view of the intramedullary rod with pivotable fastener of FIG. 1 taken along the line 2-2 of FIG. 1.

FIG. 5 is an exploded view of the head of the intramedullary rod with pivotable fastener of FIG. 1.

FIG. 6 is a side exploded view of the head of the intramedullary rod with pivotable fastener of FIG. 1 taken along the line 6-6 of FIG. 5.

FIG. 7 is a front view of the nail of the intramedullary rod with pivotable fastener of FIG. 1 with the components of the actuation mechanism removed.

FIG. 8 is a side view of the nail of FIG. 7 taken along the line 8-8 of FIG. 7.

FIG. 9 is a cross-sectional view of the nail of FIG. 7 taken along the line 9-9 of FIG. 7.

FIG. 10 is a cross-sectional view of the proximal portion of the nail of FIG. 7 taken along the line 10-10 of FIG. 8.

FIG. 11 is a side view of the head of the nail of FIG. 7 taken along the line 11-11 of FIG. 10.

FIG. 12 is an top end view of the nail of FIG. 7 taken along the line 12-12 of FIG. 11.

FIG. 13 is a cross-sectional view of the proximal portion of the nail of FIG. 7 taken along the line 13-13 of FIG. 12.

FIG. 14 is a perspective view of the insert of the intramedullary rod with pivotable fastener of FIG. 1.

FIG. 15 is a top view of the insert of FIG. 14 taken along the line 15-15 of FIG. 14.

FIG. 16 is an end view of the insert of FIG. 14 taken along the line 16-16 of FIG. 15.

FIG. 17 is a cross-sectional view of the insert of FIG. 14 taken along the line 17-17 of FIG. 16.

FIG. 18 is a perspective view of the end nut of the intramedullary rod with pivotable fastener of FIG. 1.

FIG. 19 is a side view of the end nut of FIG. 18 taken along the line 19-19 of FIG. 18.

FIG. 20 is bottom end view of the end nut of FIG. 18 taken along the line 20-20 of FIG. 18.

FIG. 21 is top end view of the end nut of FIG. 18 taken along the line 21-21 of FIG. 19.

FIG. 22 is a cross-sectional view of the end nut of FIG. 18 taken along the line 22-22 of FIG. 21.

FIG. 23 is a perspective view of the spindle of the intramedullary rod with pivotable fastener of FIG. 1.

FIG. 24 is a side view of the spindle of FIG. 23 taken along the line 24-24 of FIG. 23.

FIG. 25 is top end view of the spindle of FIG. 23 taken along the line 25-25 of FIG. 24.

FIG. 26 is bottom end view of the spindle of FIG. 23 taken along the line 26-26 of FIG. 24.

FIG. 27 is a cross-sectional view of the spindle of FIG. 23 taken along the line 27-27 of FIG. 25.

FIG. 28 is a perspective view of the set screw of the intramedullary rod with fastener of FIG. 1.

FIG. 29 is a side view of the set screw of FIG. 28 taken along the line 29-29 of FIG. 28.

FIG. 30 is an end view of the set screw of FIG. 28 taken along the line 30-30 of FIG. 29.

FIG. 31 is a cross-sectional view of the set screw of FIG. 28 taken along the line 31-31 of FIG. 30.

FIG. 32 is a perspective view of the fastener of the intramedullary rod with fastener of FIG. 1.

FIG. 33 is a side view of the fastener of FIG. 32 taken along the line 33-33 of FIG. 32.

FIG. 34 is an end view of the fastener of FIG. 32 taken along the line 34-34 of FIG. 33.

FIG. 35 is a cross-sectional view of the fastener of FIG. 32 taken along the line 35-35 of FIG. 34.

FIG. 38 is a front view of another embodiment of an intramedullary rod with pivotable fasteners of the present invention.

FIG. 39 is a side view of the intramedullary rod with pivotable fasteners of FIG. 38 taken along the line 39-39 of FIG. 38.

FIG. 41 is a perspective view of the insert of the intramedullary rod with pivotable fasteners of FIG. 38.

FIG. 42 is a top view of the insert of FIG. 41 taken along the line 42-42 of FIG. 41.

FIG. 43 is an end view of the insert of FIG. 41 taken along the line 43-43 of FIG. 42.

FIG. 44 is a cross-sectional view of the insert of FIG. 41 taken along the line 44-44 of FIG. 43.

FIG. 45 is a perspective view of the spindle of the intramedullary rod with pivotable fasteners of FIG. 38.

FIG. 46 is a side view of the spindle of FIG. 45 taken along the line 46-46 of FIG. 45.

FIG. 47 is an end view of the spindle of FIG. 45 taken along the line 47-47 of FIG. 46.

FIG. 48 is a cross-sectional view of the spindle of FIG. 45 taken along the line 48-48 of FIG. 47.

FIG. 53 is a front view of a distal portion of a further embodiment of an intramedullary rod with pivotable fasteners of the present invention.

FIG. 54 is a front view of a distal portion of a yet another embodiment of an intramedullary rod with pivotable fasteners of the present invention.

FIG. 55 is a side view of a distal portion of a yet a further embodiment of an intramedullary rod with pivotable fasteners of the present invention.

FIG. 56 is an end view of the intramedullary rod with pivotable fastener of FIG. 55 taken along the line 56-56 of FIG. 55.

DETAILED DESCRIPTION OF THE INVENTION

In general, an apparatus or device is provided for treating fractures, nonunions or malunions of the femur or other bones of a mammalian body and includes an intramedullary rod or nail and at least one fastener carried by the rod. At least one opening is provided in the head of the apparatus for slidably receiving the one or more fasteners and permitting the fastener or fasteners to pivot relative to the head of the apparatus.

Figure 3:
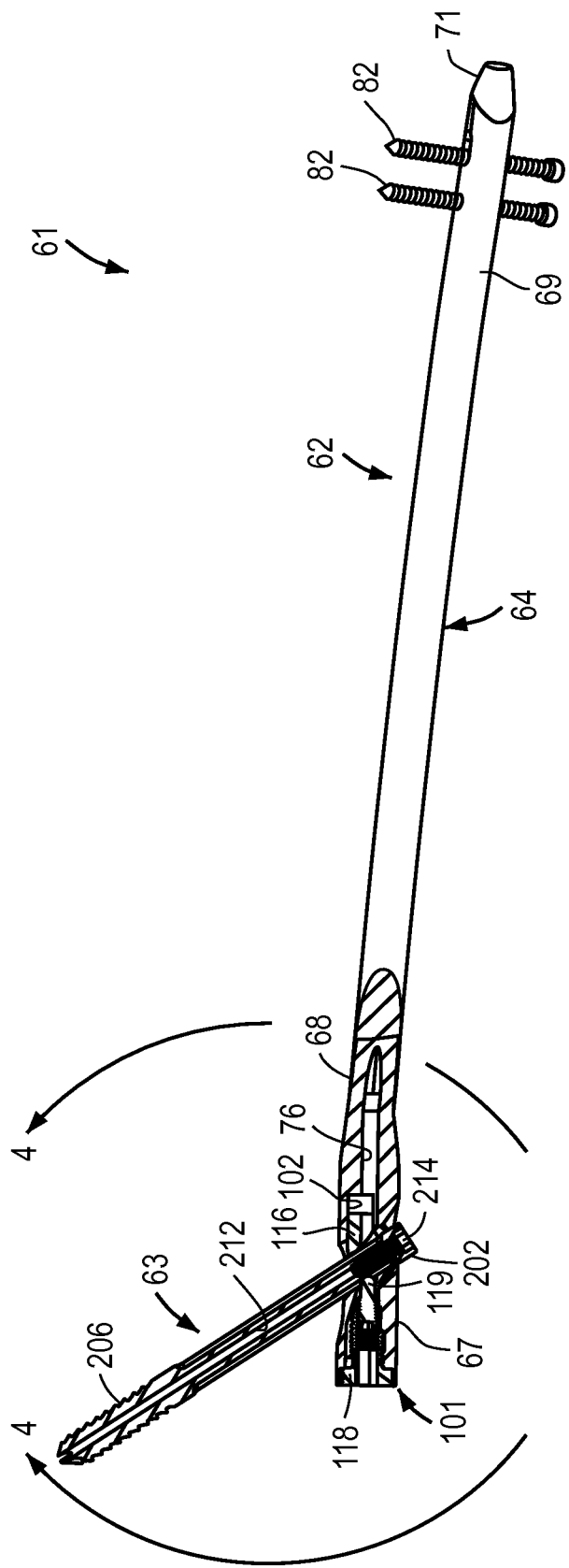
FIG. 3 is a rear view, partially sectioned, of the intramedullary rod with pivotable fastener of FIG. 1 taken along the line 3-3 of FIG. 2.

In one preferred embodiment, the apparatus 61 of the invention comprises an intramedullary rod 62 and a proximal fastener 63 pivotably carried by the proximal portion of the rod (see FIGS. 1-3). The proximal fastener 63 can be of any suitable type, including a fixation screw, a screw, a peg, a helical blade or any other fixation device, and for simplicity is referred to herein as a fixation screw. The femoral nail or rod 62 includes an elongate body 64 that extends along a longitudinal axis 66 and can have a proximal portion or head 67, a central portion or neck 68 and a distal portion or shaft 69 that terminates at a distal tip 71. The elongate body 64 may curve in at least one portion of the shaft or stem 69 to align the rod 62 along the length of the marrow canal of the femur when the rod is inserted in the femur. The elongate body 64 can be made from any suitable material such as stainless steel, titanium or another alloy and can have a length, dependent in part on the length in which the rod 62 is to be utilized, ranging from 180 to 500 centimeters. The head 67 of the nail 62 can have a length ranging from four to 15 centimeters and preferably ranging from eight to 12 centimeters and a diameter ranging from eight to 20 millimeters.

A longitudinally-extending passageway or bore 76, shown in part in FIGS. 3-4 and 9-10, can be provided and extends from a proximal opening 77 in the head 67 to an opening 78 in the tip of the stem for permitting the rod to slide along a guide wire during insertion of the rod into the femur. The curve of the longitudinal axis 66, and thus the curve of the stem 69 of the rod 62, can be through a single plane or through multiple planes. In the illustrated embodiment of nail 62, as shown in FIGS. 8, 10, 12 and 13, the curve of body 64 extends through multiple planes. At least one and in one embodiment first and second bores 81, which can extend perpendicular to the longitudinal axis 66, are provided in the distal end portion of the stem 69 adjacent the tapered tip 71 of the stem. The bores are sized to receive respective distal fasteners, such as fixation screws, screws, pegs, helical blades or any other suitable fixation devices, and in one embodiment such distal fasteners are in the form of fixation screws or screws 82 that can be fixed at an orthogonal angle relative to stem 69. In the illustrated embodiment and as shown in FIGS. 1-2 and 7-9, the distal-most bore 81 is elongated in its transverse direction, that is parallel to the longitudinal axis 66 of the stem 69, to permit the stem to be moved longitudinally relative to the respective distal fastener or fixation screw 82 before tightening of the fastener or screw to the underlying portion of the femur.

At least one transverse apertures or opening 91 is provided through the head 67 of the rod 62 and in one embodiment is angled toward the proximal end of the rod relative to longitudinal axis 66 for receiving the proximal fixation screw or fixation screw 63. More specifically, the one or more transverse apertures or holes 91 each pivotably receive a fixation screw 63 and allow for changing the angle made between the screw 63 and the nail 62. Each such aperture or first hole can extend through the head 67 in an angled direction relative to longitudinal axis 66 such that when the rod is in position within the marrow canal of the femur, axis 92 of the opening is directed toward the head of the femur (see FIG. 13). As can be seen from FIGS. 5, 6 and 10-13, the transverse aperture or aperture 91 in the head 67 can communicate with a first or lateral transverse opening 93, through which the respective fixation screw is inserted, and an opposite second or medial transverse opening 94, from which the distal portion of the screw extends. The medial transverse opening 94, as shown in FIGS. 5, 8, 11 and 13, can be elongate or oblong in a transverse direction, that is parallel to longitudinal axis 66 of head 67 and body 64, so as to accommodate pivoting of the distal portion of the proximal fixation screw 63.

Figure 4:
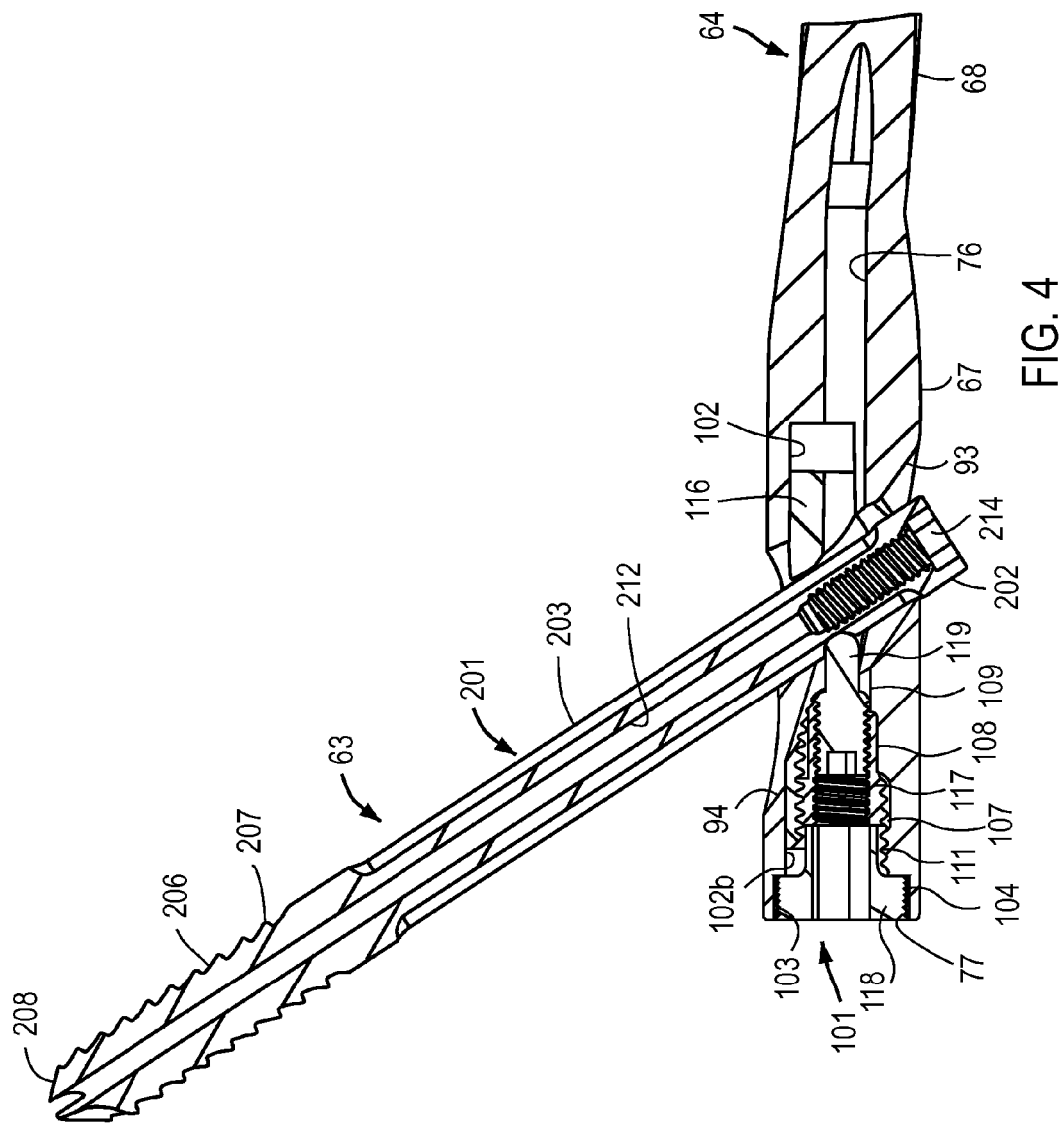
FIG. 4 is an enlarged cross sectional view of the intramedullary rod with pivotable fastener of FIG. 1 taken along the line 4-4 of FIG. 3.

The head 67 of rod 62 may include an actuation or adjustment mechanism or assembly 101 for selectively pivoting the proximal fixation screw 63 within the transverse aperture 91 (see FIGS. 4-31). In this regard, the proximal portion of the central passageway 76 of the nail 62 can be hollowed to form a longitudinally-extending proximal recess 102 in the head that communicates with a proximal opening 103 in the head. As illustrated in FIGS. 12 and 13, the recess 102 can have a proximal portion 102*a*, adjacent the proximal opening 103, and a segmented circular portion 102*b* that extends in cross section through any suitable angle preferably ranging from 180 to 240 degrees and illustrated in FIG. 12 as approximately 240 degrees, along the inside of the head 67 adjacent the medial transverse opening 94. Internal threads 104 can be provided in proximal portion 102*a*. The segmented circular portion or segmented portion 102*b* of recess 102 may be formed from an inner arcuate surface 105. The other side of the recess 102, that is the side opposite of segmented portion 102*b*, can be formed with a first shelf 107, a second shelf 108 and a third shelf 109 that can each extend further radially inwardly than the inner arcuate surface 105 of the segmented portion 102*b* and can have increasingly smaller radii relative to longitudinal axis 66 (see FIGS. 11-13). The proximal portion of the first shelf 107 can be optionally provided with internal threads 111, as shown in FIGS. 4, 9 and 10. A shoulder 112 can extend radially inwardly from first shelf 107 to second shelf 108 (see FIG. 13). The third shelf 109 may abut the lateral transverse opening 93, as shown in FIG. 11. Transversely aligned slots 110 may be provided on the proximal end of head 67 at proximal opening 103 for registering the nail 62 with an insertion jig, targeting device or other suitable device when placing or otherwise manipulating the nail within the targeted bone.

Although the actuation mechanism 101 for pivoting the proximal fixation screw 63 can be of any suitable type, in one embodiment the mechanism 101 includes an insert or sleeve 116, a spindle 117, an end or safety nut 118 and an alignment or set screw 119, as shown in the exploded views of FIGS. 5-6 and in the assembled view of FIG. 4. Each of these components can be made from any suitable material such as stainless steel.

Elongate insert or sleeve 116, as illustrated in FIGS. 14-17, may be formed from a tubular-like member 121 that can have a proximal portion 122 and a distal portion 123 and a longitudinally-extending opening 124 extending through one side. Sleeve 116 can have the shape of a cylinder with an elongate cutout 126 provided along one side thereof, opposite opening 124, that communicates with the longitudinal bore 127 extending therethrough from proximal or top end 128 and distal or bottom end 129. The planar top and bottom ends can extend parallel to each other. As such, sleeve 116 has a segmented circular or C shape when viewed from an end along its longitudinal axis, as shown in FIG. 16. Such transverse, cross-sectional configuration of sleeve 116 preferably approximates the cross-sectional configuration of the segmented circular portion 102*b* of the recess 102 in head 67 and can extend through an arc ranging from 100 to 360 degrees, preferably ranging from 180 to 240 degrees and illustrated in FIG. 16 as approximately 240 degrees. The elongate transverse opening 124 can be formed in the center of the insert. Such opening 124 may be oblong or elongate in shape and smaller than the medial transverse opening 94 provided in head 67 of the nail 62. The insert 116 may be provided with internal thread 131 extending through the bore 127 at the proximal portion 122 of the insert, such threads being adjacent the top or proximal end of the insert as shown in FIGS. 14 and 17. The insert can have a length ranging from 30 to 110 millimeters and can have an external radius sized to fit within head 67 of the nail 62. The distal portion of internal bore 127, that is the portion of the bore distal transverse opening 124, has a smaller internal diameter than the internal diameter of the proximal portion of the bore.

Spindle 117 can be formed from a cylindrical body 136 provided with a distal portion 137 of constant radius and can have a smooth outer cylindrical surface 138, a central portion 139 adjacent the distal portion and having external threads 141 extending radially outwardly relative to the distal portion and a proximal or neck portion 142 adjacent the central portion (see FIGS. 18-22). The neck portion can include a proximal flange 143 and an annular recess 144 disposed between the flange and the central portion 139 of the spindle 117. The cylindrical body can further include a proximal or top end 147 and a distal or bottom end 148, as shown in FIG. 22. The planar ends 148 and 148 may extend parallel to each other. A central passageway or bore 151 can extend through the spindle. The distal portion of the central passageway may be provided with internal thread 152 and the proximal portion of the central passageway may be provided with any suitable cross-sectional configuration for serving as a drive socket 153. The spindle can have a length ranging from five to 50 millimeters and preferably approximately 15 millimeters.

End nut 118 can be formed from a cylindrical body 161 provided with a distal portion 162 of constant radius and a smooth outer surface 163 and a proximal portion 164 adjacent the distal portion and having external threads 166 extending radially outwardly relative to the distal portion (see FIGS. 23-27). The cylindrical body can further include a proximal or top end 167 and a distal or bottom end 168, as shown in FIG. 27. Planar ends 167 and 168 can extend parallel to each other. A central passageway or bore 171 can extend longitudinally through the end nut between ends 167 and 168 and at least the proximal portion of the bore 171 can be provided with any suitable cross-sectional configuration for serving as a drive socket. The distal end portion of the end nut may be provided with a recess or socket 172, that can be in communication with bore 171 and be side opening onto the outer cylindrical surface 163 of the distal portion 162. The socket 172 can be sized and configured for cooperatively receiving the neck portion 142 of the spindle 117 and may include a partial annular flange 173, shown most clearly in FIG. 24, extending radially inwardly for partially seating in the annular recess 144 of the spindle and a partial annular recess 174 extending radially outwardly relative to the flange for receiving part of the proximal, annular flange 143 of the spindle. The end nut can have a length ranging from five to 50 millimeters and preferably approximately 15 millimeters.

Set screw 119 can be formed from a cylindrical body 181 provided with a distal portion 182 of constant radius and a smooth outer surface 183 and a proximal portion 184 adjacent the distal portion and having external threads 186 extending radially outwardly relative to the distal portion (see FIGS. 28-31). The cylindrical body 181 can further include a proximal or top end 187 and a distal or bottom end 188, as shown in FIG. 29. A drive socket 191 of any suitable cross-sectional configuration may extend longitudinally through at least a portion of the cylindrical body and open at the top end 187 of the body. The bottom end 188 of the body can be blunted. The set screw can have a length ranging from five to 60 millimeters and preferably approximately 20 millimeters.

Proximal fastener 63 for use in the head 67 of the intramedullary rod 62 can be of any suitable type and in one embodiment is made from an elongate cylindrical body 201 or spiral blade (not shown) having a length ranging from 40 to 200 millimeters and a diameter ranging from two to 20 millimeters (see FIGS. 32-35). In the illustrated embodiment, the fastener is a fixation screw formed from a body having a threaded portion and a smooth portion. The elongate body 201 can be formed from any suitable material such as stainless steel and include a proximal portion 202 having any outer cylindrical or irregular-shaped surface 203. The proximal portion 202 may be provided with a plurality and as shown four longitudinally-extending slots 204 extending through the surface 203 in circumferentially-spaced apart positions. Distal portion 206 of the body 201 may be provided with external threads 207 that extend to a sharpened distal end or tip 208 of the body. Alternatively, the distal portion 206 of the body 201 may be irregularly shaped or flat (not shown). The body can further have a proximal end 211 and be provided with a central bore 212 that extends longitudinally through the body from the proximal end 211 to the distal end 208 (see FIG. 35). The proximal end of the central bore 212 may be provided with internal threads 213 and be formed with a drive socket 214 of any suitable type for facilitating connection of the proximal fixation screw to a drive tool of any suitable type.

Actuation assembly or mechanism 101 loaded into the head 67 of the nail 62 in any suitable manner. In one method of assembly, insert or sleeve 116 is slidably inserted through the proximal opening 103 of the head and slidably seated in the segmented circular portion 102b of the recess 102 in the head. The transverse opening 124 in the insert 116 is in general registration with the medial transverse opening 94 in the head 67. The proximal or neck portion 142 of spindle 117 is seated in the socket 172 formed in the distal portion 162 of end nut 118 so that the end nut and spindle are coaxial along the central longitudinal axes of the end nut and spindle. The combined spindle 117 and end nut 118 assembly are loaded into the head 67 by introducing the distal portion 137 of the spindle into the proximal opening 103 in the head. A suitable drive tool (not shown) can be used to engage the drive socket in the central bore 171 at the proximal portion 164 of the end nut to rotate the end nut within the internal threads 104 adjacent the proximal opening 103 in the head so as to move the end nut 118, and the spindle 117 captured thereby, longitudinally into the recess 102 of the head until the spindle seats is the distal portion of the first shelf 107 against shoulder 112 extending between the first shelf 107 and the second shelf 108. As spindle 117 is moved distally within the recess 102 of the head 67, the external threads 141 of the spindle engage the internal threads 131 on the proximal portion 122 of insert 116. The spindle can be moved longitudinally into threaded engagement with the insert by engagement of the drive socket 153 in the proximal or neck portion 142 of spindle 117 with a suitable drive tool and clockwise rotation of the spindle within the recess 102 of the head 67.

The set screw 119 can thereafter be introduced through central bore 171 of the end nut 118 and into central bore 151 of the spindle 117 until the external threads 186 provided on the proximal end portion 184 of the set screw engage the internal threads 152 provided within the distal portion 137 of the spindle. A suitable drive tool may be used to engage the drive socket 191 in the proximal portion 184 of the set screw 119 to move the set screw distally relative to the spindle 117 by the rotational engagement of the external threads 186 on the set screw with the internal threads 152 of the spindle. The distal portion 182 of the set screw can thus be moved distally of the spindle 117 into the transverse aperture 91 in head 67 of the nail 62.

Figure 36:
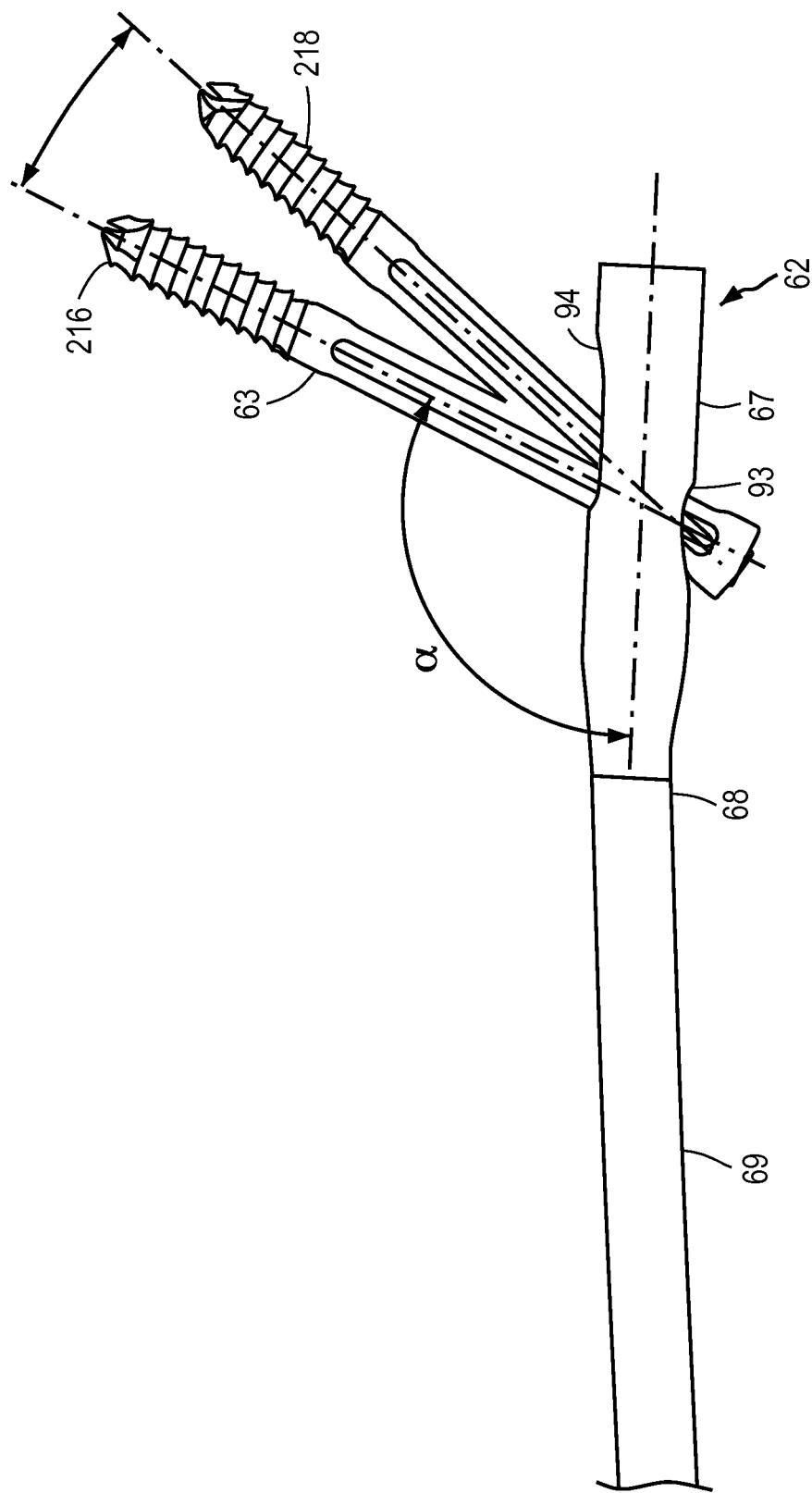
FIG. 36 is a front view of the proximal portion of the intramedullary rod with pivotable fastener of FIG. 1 showing the fastener in the first position of FIG. 1 relative to the intramedullary rod and the fastener in a second position relative pivoted counterclockwise to the intramedullary rod.
Figure 37:
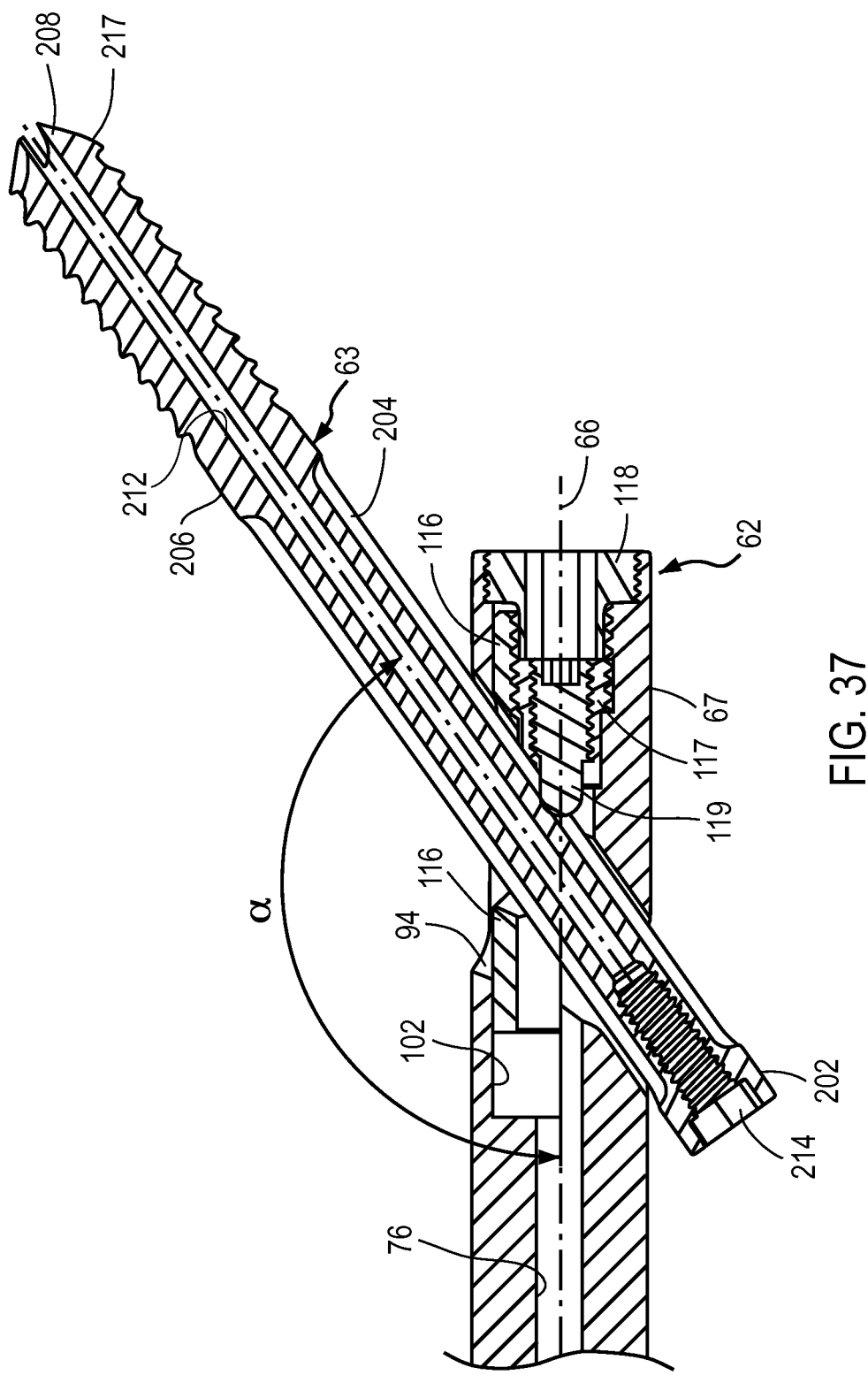
FIG. 37 is a cross-sectional view of the proximal portion of the intramedullary rod and pivotable fastener of FIG. 1 showing the fastener in a third position relative to the intramedullary rod.

Upon insertion of the proximal fixation screw 63 into the transverse aperture 91 of the head 67, and through the transverse opening 124 in the insert 116, the fixation screw can be pivoted about a transverse axis of the head through an angle of up to 70 degrees and preferably approximately 30 degrees relative to the nail 62. In one embodiment, illustrated in the figures, the fixation screw 63 is pivotable between a first position 216, extending at an angle α of approximately 115 degrees relative to the stem 69 of the nail and shown in FIG. 36, and a second position 217, extending at an angle α of approximately 145 degrees relative to the stem of the nail and shown in FIG. 37. The fixation screw is shown in an intermediate position 218, extending at an angle α of approximately 130 degrees relative to the stem of the nail, in FIG. 36. To so pivot the fixation screw, in one procedure the physician rotates the spindle 117 within the head 67, for example by engaging the drive socket 153 in the neck portion 142 of the spindle with a suitable drive tool, so that the external threads 141 on the central portion 139 of the spindle that engage the internal threads 131 within the insert 116 cause the insert to move proximally within the head from a first or distal position in the segmented circular portion (not shown) to a second or proximal position in the segmented circular portion, illustrated in FIG. 37. The distal end of the transverse opening 124 in the insert 116 engages the fixation screw during proximal movement of the insert within the head 67 to cause the fixation screw to pivot within the lateral transverse opening 93 of the transverse aperture 91 of the head. When in its operational position within the head 67, shown in FIG. 37, the spindle 117 can rotate freely relative to the head and the end cap 118. The set screw 119 can be rotated distally with the spindle 117 so that the blunted end 188 of the set screw seats within one of the longitudinal slots 294 formed in the proximal portion 202 of the fixation screw 63 so as to rotatably lock the fixation screw relative to the head 67 of the intramedullary rod 62 and thus inhibit undesirable further advancement or withdrawal of the screw 63 relative to the rod 62.

Although the actuation mechanism 101 of intramedullary rod 62 has been shown and described with a longitudinally movable insert or sleeve 116 disposed within the nail, it is appreciated that an insert or sleeve slidably disposed on the outside of the nail 62 can be provided for pivoting the fixation screw 62 relative to the nail.

It is further appreciated that other embodiments of the intramedullary rod of the present invention, for example with any plurality of pivotable fasteners can be provided. Another apparatus 231 is illustrated in FIGS. 38-52 and can includes an intramedullary rod 232 substantially similar to rod 62. Like reference numerals have been utilized to describe like components of rods 62 and 232. The intramedullary rod 232 has any suitable first and second proximal fasteners, shown as first and second proximal fixation screws 233 and 234 that can each be substantially identical to proximal fixation screw 63, pivotably received within respective first and second transverse apertures 236 and 237 that can each be substantially identical to transverse aperture 91 and extend along respective axes 92. The first and second fasteners 233 and 234 extend parallel to each other, may or may not be of the same length and may or may not be of the same type of fastener. For example, the first fastener 233 may be a screw and the second fastener 234 may be a peg or blade. The apertures 236 and 237 are provided in a head 239, substantially similar to head 67, of the rod 232.

An actuation mechanism or assembly 241, substantially similar to actuation mechanism 101, can be provided with the head 239 of the rod 232. Actuation mechanism 241, shown in an assembled position in FIG. 40, can include an insert or sleeve 242 substantially similar to the insert 116 of mechanism 101 but having first and second transverse apertures 246 and 247 similar to transverse aperture 91 of the sleeve 116 and extending at an angle to the longitudinal axis of the nail for respectively receiving and pivoting the first and second fixation screws 233 and 234 (see FIGS. 41-44). The axes 92 of the first and second transverse apertures 246 and 247 can be parallel to each other but may also not be parallel to each other. The insert 242 can have a length ranging from 20 to 120 millimeters and an external radius sized to fit within head 239 of the nail 232. A spindle 256 can be provided that is substantially similar to the spindle 117 but formed without the distal portion 137 of spindle 117 (see FIGS. 45-48). Instead, spindle 256 of the dual fixation screw rod 232 of FIGS. 38-52 has a proximal or neck portion 142 and a distal portion 257 substantially similar to central portion 139 of the spindle 117. The spindle 256 can have a length ranging from five to 30 millimeters. An end cap or nut 266 substantially similar to end nut 118 but shorter in length can be further provided (see FIGS. 49-51). The end nut can have a length ranging from three to 30 millimeters. The proximal portion 142 of spindle 256 is shown as being captured or seated in socket 172 in the distal portion 162 of end nut 266 in FIG. 52 so that the spindle and end cap are coaxially aligned in their operational positions relative to each other.

Figure 40:
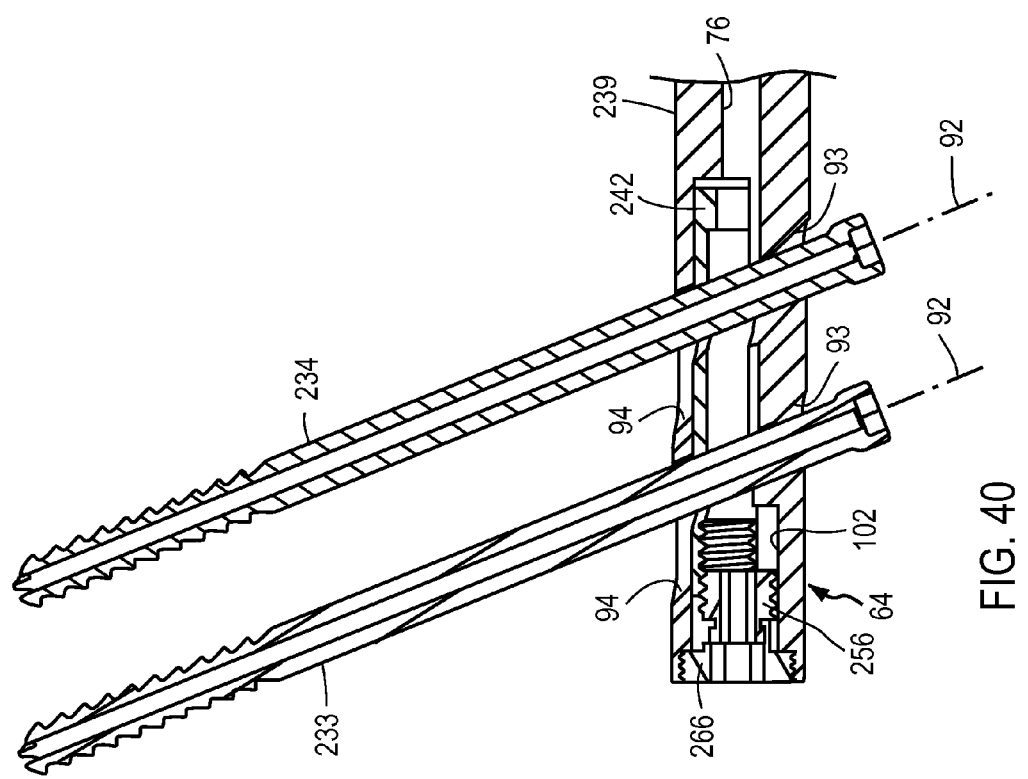
FIG. 40 is a cross-sectional view of the intramedullary rod with pivotable fasteners of FIG. 38 taken along the line 40-40 of FIG. 39.
Figure 50:
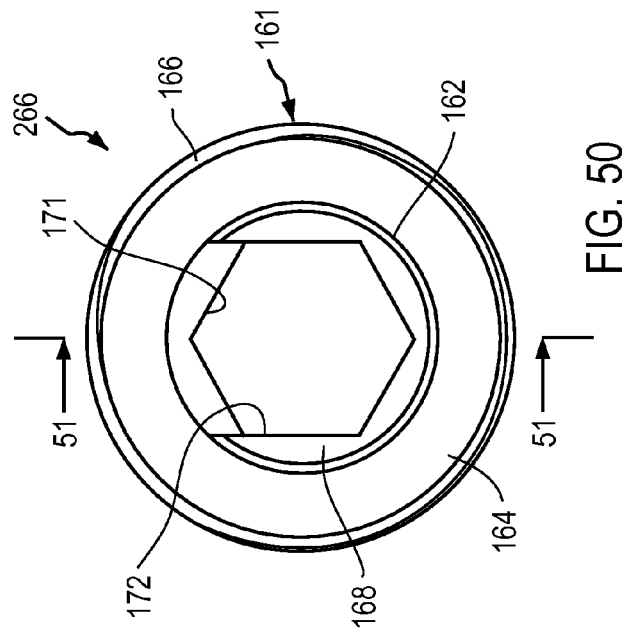
FIG. 50 is an end view of the set screw of FIG. 49 taken along the line 50-50 of FIG. 49.
Figure 49:
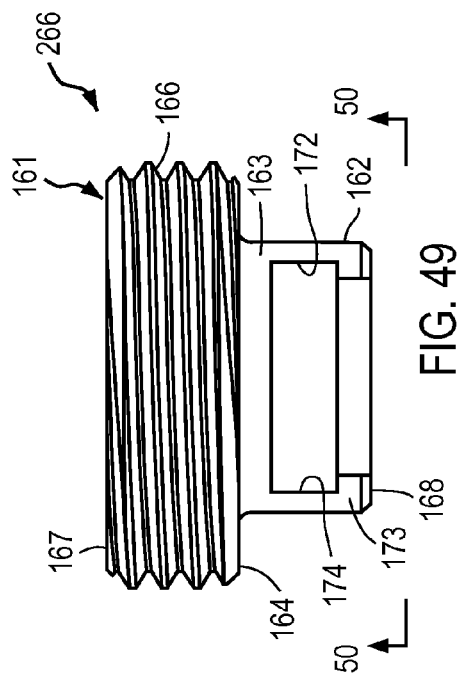
FIG. 49 is a side view of the set screw of the intramedullary rod with pivotable fasteners of FIG. 38.
Figure 51:
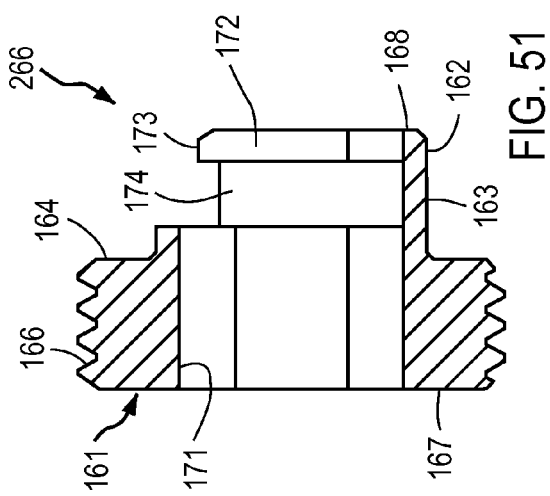
FIG. 51 is a cross-sectional view of the set screw of FIG. 49 taken along the line 51-51 of FIG. 50.
Figure 52:
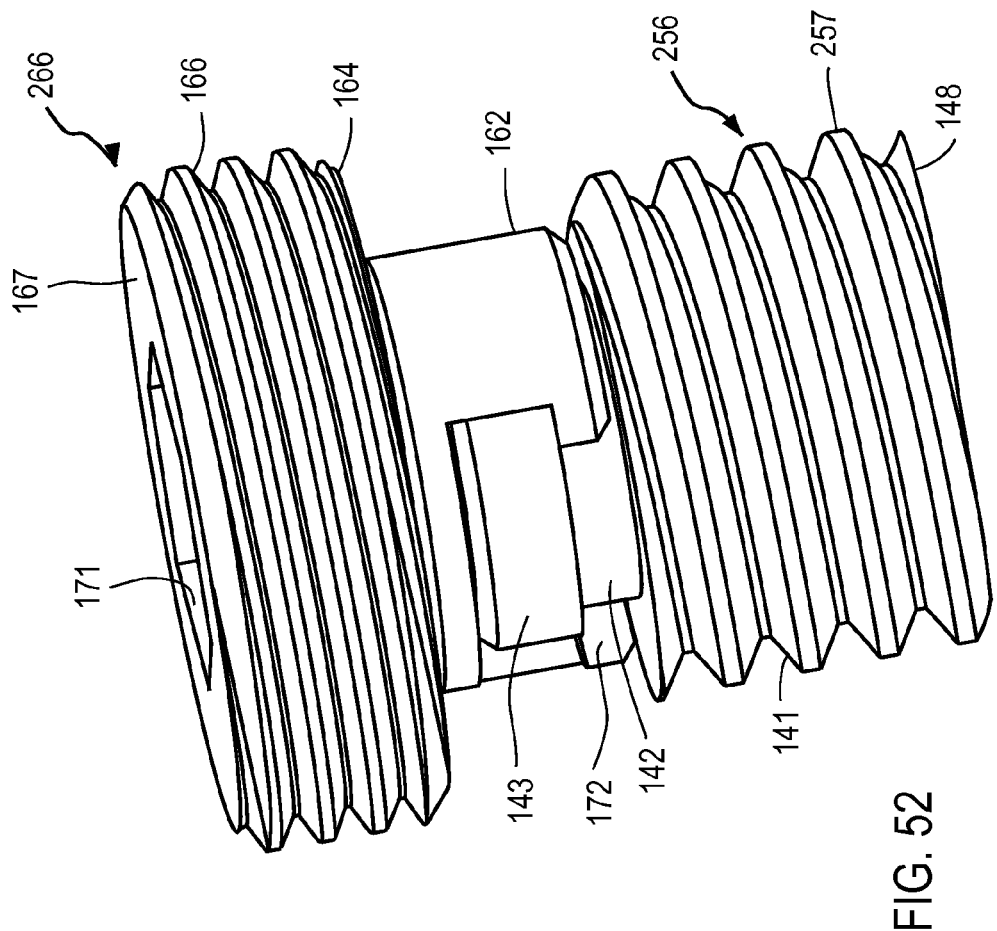
FIG. 52 is a perspective view of the set screw of FIG. 49 mounted on the spindle of FIG. 45.

The components of actuation assembly 241 can be loaded into head 239 of dual fixation screw rod 232, and operated therein with respect to first and second proximal fixation screws 233 and 234, in substantially the same manner as discussed above with respect to apparatus 61. Sleeve 242 is shown in FIG. 40 in its distal position. The inclusion in apparatus 241 of the second fixation screw 234 minimizes the need for a set screw, such as set screw 119, and preferably eliminates the need for such a set screw. In this regard, the second proximal fixation screw is included in the means or mechanism of the rod 232 for preventing rotation of the head of the femur relative to the first proximal fixation screw 233 during use of rod 232. It is appreciated that other means, such as a nail, peg, blade or bolt, can be included in an intramedullary rod of the present invention for inhibiting rotation of the head of the femur relative to the first fixation screw. The optional second aperture 237 and second proximal fixation screw 234 allow sliding compression so as to prevent rotation and to adapt the apparatus or device to a variety of applications.

A further embodiment of the intramedullary rod with pivotable fasteners of the present invention is illustrated in FIG. 53 wherein an apparatus 271 substantially similar to apparatus 61 and 231 is provided. Like reference numerals have been used to describe like components of apparatus 61, 231 and 271. Intramedullary rod or nail 272 of the apparatus 271 is substantially similar to rods 62 and 232 and has any suitable first and second proximal fasteners, shown as first and second proximal fixation screws 233 and 234. The first screw 233 is pivotably received within first transverse aperture 236 extending along axis 92. The second screw 234 is pivotably received within a second transverse aperture 273 extending along an axis 274. The aperture 273 can be substantially identical to transverse aperture 236 except that axis 274 of the second transverse aperture 273 is not parallel to the axis 92 of the first transverse aperture 236. The first and second fasteners 233 and 234 extend nonparallel to each other, may or may not be of the same length and may or may not be of the same type of fastener. The apertures 236 and 273 are provided in a head 276 of the rod 272 that is substantially similar to head 239 of rod 232. An actuation mechanism or assembly (not shown) substantially similar to actuation mechanism 241 but modified to provide for the nonparallel disposition of apertures 236 and 273 is provided.

Another embodiment in the form or apparatus 281 is illustrated in FIG. 54 and can include an intramedullary rod 282 substantially similar to rods 62 and 232. Like reference numerals have been utilized to describe like components of rods 62, 232 and 282. The intramedullary rod 282 has any suitable first, second and third proximal fasteners, shown as first, second and third proximal fixation screws 233, 234 and 283, pivotably received within respective first, second and third transverse apertures 236, 237 and 286. The third proximal fixation screw 283 can be identical to one or both of first and second proximal fixation screws 233 and 234, and the third transverse aperture 286 can be identical to one or both of first and second transverse apertures 236 and 237. The first, second and third fasteners 233, 234 and 283 may or may not extend parallel to each other, may or may not be of the same length and may or may not be of the same type of fastener. In the illustrated embodiment, the fasteners 233, 234 and 283 extend parallel to each other. The apertures 236, 237 and 286 are provided in a head 287 of the rod 282 that is substantially similar to head 239 of rod 232. An actuation mechanism or assembly (not shown) substantially similar to actuation mechanism 241 but modified to provide for the third transverse aperture 286 can be provided.

Yet a further embodiment of the intramedullary rod with pivotable fasteners of the present invention is illustrated in FIGS. 55-56 wherein an apparatus 296 substantially similar to apparatus 61 and 231 is provided. Like reference numerals have been used to describe like components of apparatus 61, 231 and 296. Intramedullary rod or nail 297 of the apparatus 296 is substantially similar to rods 62 and 232 and has any suitable first and second proximal fasteners, shown as first and second proximal fixation screws 233 and 234. The first screw 233 is pivotably received within first transverse aperture 236 extending along axis 92. The second screw 234 is pivotably received within a second transverse aperture 298 extending along an axis 299. The second transverse aperture 298 can be substantially identical to the first transverse aperture 236 except that axis 299 of the second transverse aperture 298 is not parallel to the axis 92 of the first transverse aperture 236. More specifically, axis 299 is circumferentially angled about the longitudinal axis 66 of rod 297 relative to axis 92, as shown in FIG. 56 by, angle $\theta$. Angle $\theta$ can be any suitable number. Axes 92 and 299 can extend at the same angle relative to longitudinal axis 66, such as axes 92 of rod 232 as shown in FIG. 38, or can extend at different angles relative to longitudinal axis 66, such as axes 92 and 274 of rod 272 as shown in FIG. 53. The first and second fasteners 233 and 234 may or may not be of the same length and may or may not be of the same type of fastener. The apertures 236 and 298 are provided in a head 301 of the rod 297 that is substantially similar to head 239 of rod 232. An actuation mechanism or assembly (not shown) substantially similar to actuation mechanism 241 but modified to provide for the different circumferential alignment of apertures 236 and 298 is provided.

It can be seen from the foregoing various embodiments of the intramedullary rod with pivotable fasteners of the present invention that such fasteners can be of any suitable number. Where multiple fasteners are provided, the fasteners can extend parallel to each other or at various angles to each other relative to the longitudinal axis and about the longitudinal axis of the nail. Extrapolations of the illustrated apparatus can be provided, for example where three nonparallel fasteners are provided, where multiple fasteners are circumferentially aligned relative to each other about the longitudinal axis of the rod but spaced the same distance from the proximal end of the rod or where two or more first fasteners are circumferentially aligned relative to such longitudinal axis and one or more second fasteners are circumferentially spaced apart about such longitudinal axis relative to the first fasteners.

Although the apparatus of the invention has been illustrated as having a separate transverse aperture in the rod for each fastener, it is appreciated that multiple fasteners can pivotably extend through a single transverse aperture. In one such embodiment in which a single transverse aperture receives two fasteners, one or both of the aperture in the rod and the aperture in the actuation mechanism has a configuration that narrows between two end portions of such aperture such that the two fasteners extending through respective end portions of such aperture are separated from each other by the narrowed material of the rod and/or the actuation mechanism.

Figure 57:
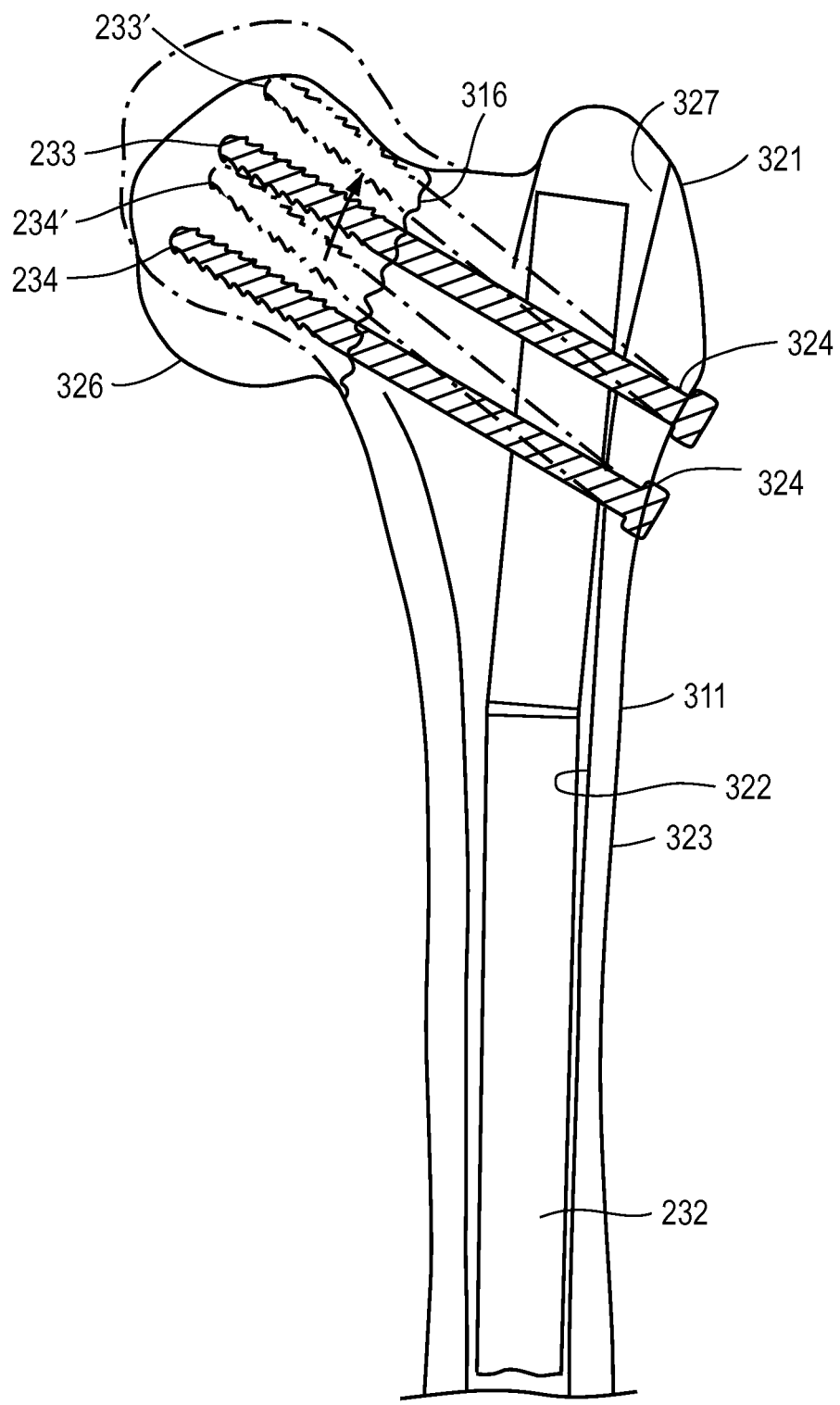
FIG. 57 is a schematic front view of the intramedullary rod with pivotable fasteners of FIG. 38 disposed in a femur to repair a femoral neck fracture.
Figure 58:
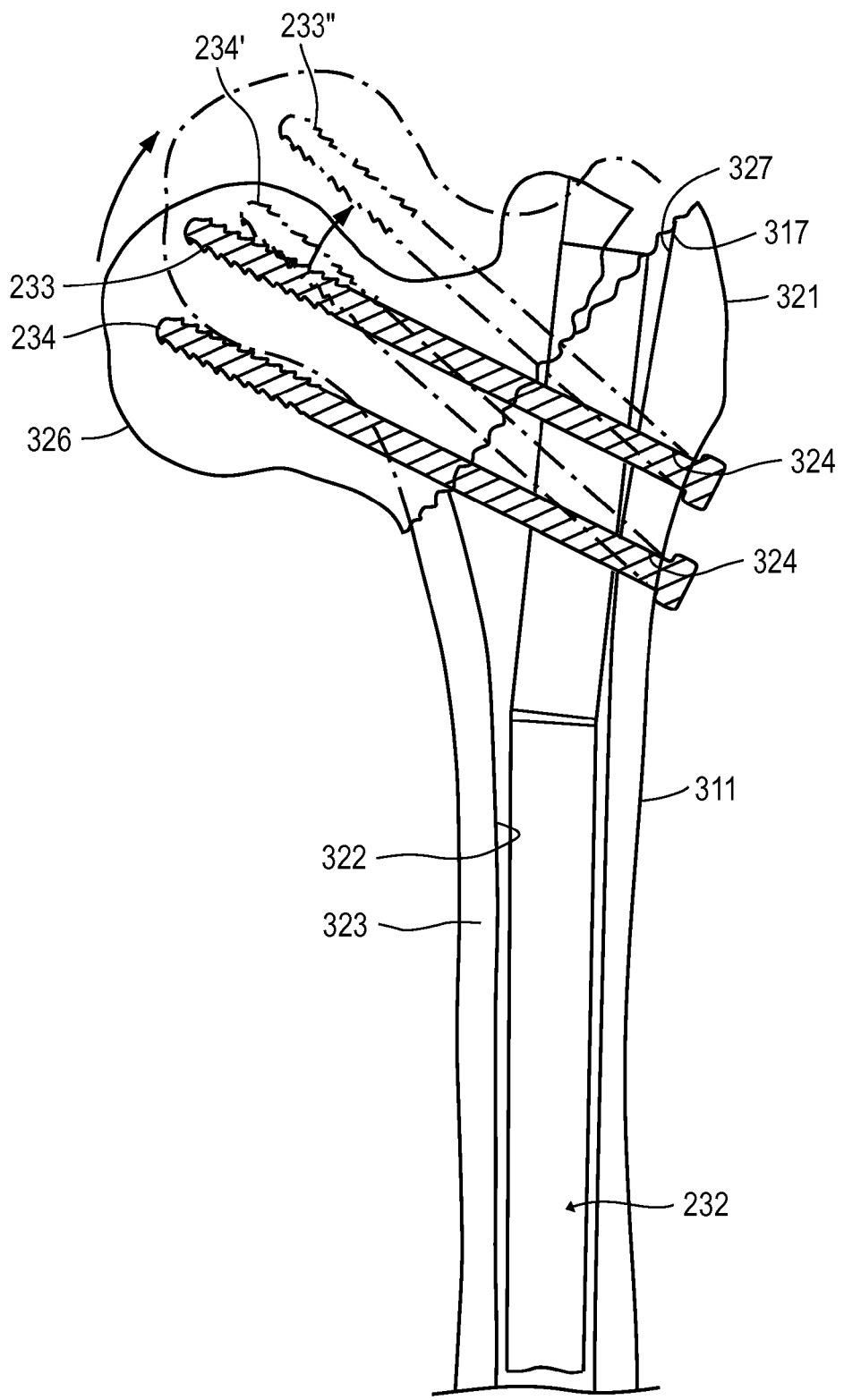
FIG. 58 is a schematic front view of the intramedullary rod with pivotable fasteners of FIG. 38 disposed in a femur to repair an intertrochanteric fracture.
Figure 59:
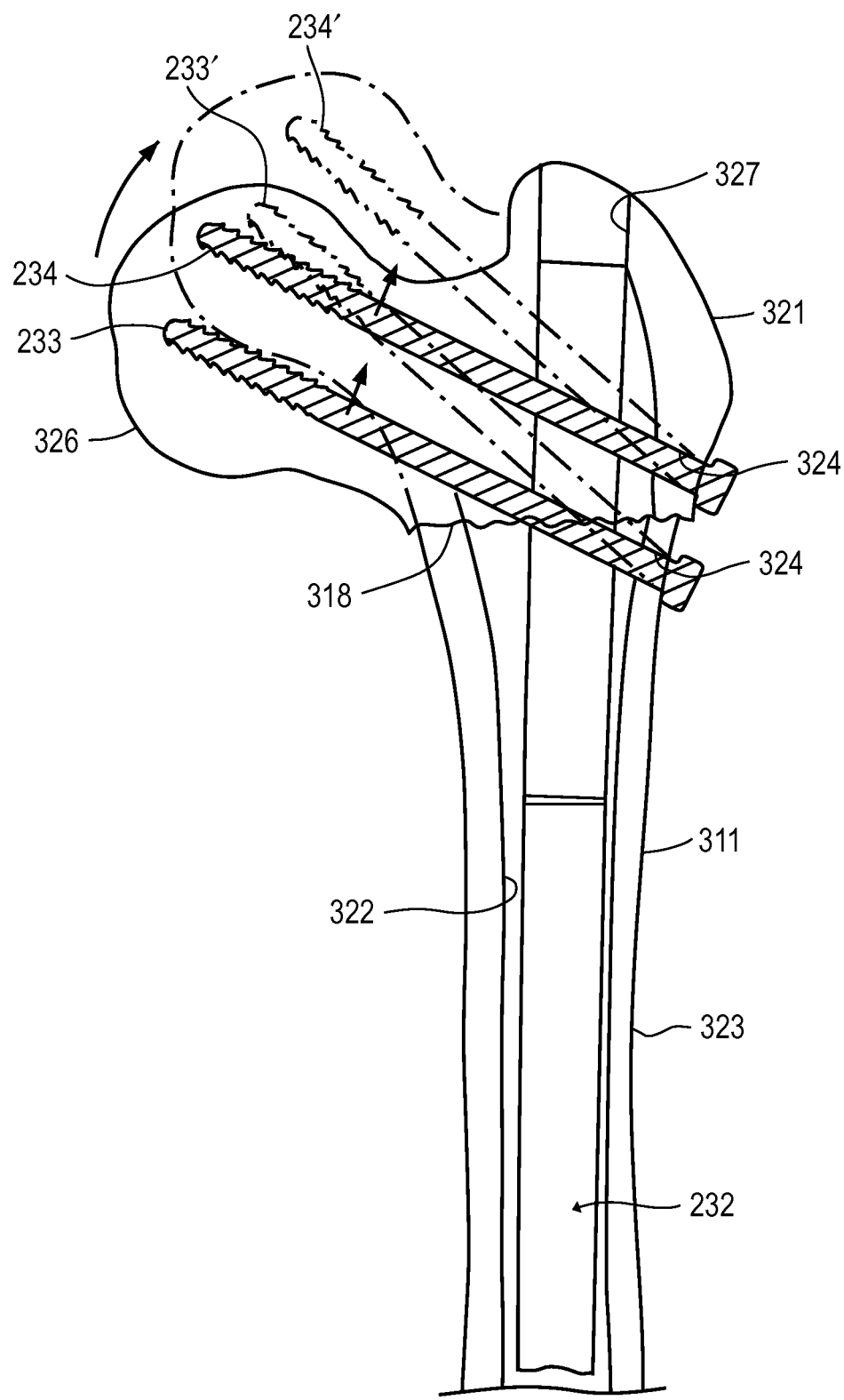
FIG. 59 is a schematic front view of the intramedullary rod with pivotable fasteners of FIG. 38 disposed in a femur to repair a subtrochanteric fracture.

Several procedures for utilizing the intramedullary rod with pivotable fixation screws of the present invention are illustrated in FIGS. 57-59, where apparatus 231 with dual fixation screw rod 232 is shown in use to repair peritrochanteric fractures of a femur 311. More specifically, 232 rod is shown repairing a femoral neck fracture 316, an intertrochanteric fracture 317 and a subtrochanteric fracture 318, respectively, in FIGS. 57-59. Previous to the procedure of the invention, the rod 233 was introduced through the greater trochanter 321 into the medullary canal 322 in the shaft 323 of the femur. Suitable holes 324 were made in the side of the greater trochanter to allow insertion of the first and second fixation screws 233 and 234 into the lateral transverse openings 93 of the respective first and second transverse apertures 236 and 237 in the head 239 of the rod. The fixation screws were thereafter screwed into the head 326 of the femur 311. In each instance, however, further adjustment of the head of the femur may be required either because the fracture is malreduced, the entry point for the rod in the greater trochanter was too lateral or a combination of the foregoing. In one procedure of the invention, a suitable drive (not shown) element is introduced through the entry point 327 in the femur into the proximal opening 103 in the head 239 of the nail 232 and through the end nut 266 so as to seat within the drive socket 153 in the neck portion 142 of the spindle 256. The spindle 256 is rotated by the drive element, for example in a clockwise direction, so that the external threads 141 on the spindle engaged with the internal threads 131 on the proximal portion 122 of the insert or sleeve 242 and cause the insert 242 to slide or move proximally within the head 239 and thus cause each of the first and second proximal fixation screws 233 and 234 to pivot upwardly toward the head 239 of the rod, that is in a clockwise direction in FIGS. 57-59, until the fracture is reduced and the head 326 of the femur 311 is brought out of varus and thus properly positioned relative to the remainder of the femur, as shown in phantom lines in FIGS. 57-59. The first and second proximal fixation screws are identified as 233' and 234' in FIGS. 57-59 when in their second position in which they have been pivoted upwardly toward the head 239 of the rod 232.

The capture of the neck portion 142 of the spindle 256 in the socket 172 of the end nut 266 inhibits movement of the spindle 256 from its coaxial position with the longitudinal axis of the head 239 and thus inhibits undesirable movement of the insert 242, and the first and second fixation screws 233 and 234 retained in position by the insert, that may result from such misalignment of the spindle 256 in the head 239 of the rod. The second fixation screw 234 inhibits, if not prevents, rotation of the femoral head 326 relative to the first fixation screw 233.

It is appreciated that the apparatus of the invention can include more than two proximal fasteners to fixate head 326 of the femur, or a portion of any other suitable bone, and be within the scope of the present invention.

As can be seen from the foregoing, an apparatus has been provided for treating fractures of the femur that marries the fixation attributes of an intramedullary nail with the benefits of a sliding compression screw. The apparatus provides a single device for treating a variety of femoral fractures, which heretofore have required more than one device. The device can be used to treat a variety of femoral fractures and femoral osteotomies and permits hospitals and manufacturers to reduce the variety of inventories of orthopedic surgical devices and thereby reduce costs. The device allows physicians to move the fracture or osteotomy to a more favorable position after implantation, and for example allows sliding compression of a femoral neck or intertrochanteric fracture. The apparatus permits the physician to vary the angle of the proximal fixation screws extending into the head of the femur, which can be done before insertion or after insertion of the femoral rod into the femoral intramedullary canal.

What is claimed is:

1. An intramedullary rod for use with a fastener to repair a bone in a mammalian body comprising an elongate nail extending along a central longitudinal axis and having a stem and a head, the head being provided with an aperture extending at an angle to the central longitudinal axis and adapted to receive the fastener, the aperture having opposite first and second side portions spaced from the central longitudinal axis, and a mechanism carried by the head for engaging the fastener in the first side portion of the aperture so as to pivot the fastener about a transverse axis spaced from the central longitudinal axis in the second side portion of the aperture from a first angled position relative to the head to a second angled position relative to the head.

2. The intramedullary rod of claim 1 for use with an additional fastener wherein the head is provided with an additional aperture extending at an angle to the longitudinal axis and adapted to receive the additional fastener, the additional aperture having opposite first and second side portions spaced from the central longitudinal axis, the mechanism being configured to engage the additional fastener in the first side portion of the additional aperture so as to pivot the fastener about an additional transverse axis spaced from the central longitudinal axis in the second side portion of the additional aperture from a first angled position to a second angled position relative to the head.

3. The intramedullary rod of claim 2 wherein the aperture and the additional aperture extend parallel to each other.

4. The intramedullary rod of claim 2 wherein the aperture and the additional aperture do not extend parallel to each other.

5. The intramedullary rod of claim 2 wherein the aperture and the additional aperture are circumferentially spaced apart about the longitudinal axis from each other.

6. The intramedullary rod of claim 1 wherein the mechanism is disposed within the head.

7. The intramedullary rod of claim 6 wherein the head is provided with a proximal opening along the longitudinal axis for permitting adjustment of the mechanism in situ.

8. An intramedullary rod for use with a fastener to repair a bone in a mammalian body comprising an elongate nail extending along a longitudinal axis and having a stem and a head, the head being provided with an aperture extending at an angle to the longitudinal axis and adapted to receive the fastener, and a mechanism carried by the head of the nail for pivoting the fastener from a first angled position relative to the head to a second angled position relative to the head, the head of the nail including a proximal end and the mechanism including a control element carried by the head of the nail and accessible at the proximal end for causing the mechanism to pivot the fastener in situ.

9. The intramedullary rod of claim 8 wherein the mechanism is disposed in the head.

10. The intramedullary rod of claim 8 wherein the control element includes a screw.

11. An intramedullary rod for use with a fastener and a guide wire to repair a bone in a mammalian body comprising an elongate nail extending along a longitudinal axis and having a stem and a head, the head being provided with an aperture extending at an angle to the longitudinal axis and adapted to receive the fastener, and a mechanism carried by the head for pivoting the fastener from a first angled position relative to the head to a second angled position relative to the head, the elongate nail including a longitudinally-extending passageway and the mechanism including a longitudinal bore inclined relative of the aperture for receiving the guide wire and thus permitting the elongate nail and mechanism to slide over the guide wire when being introduced into the bone.

12. The intramedullary rod of claim 11 wherein the mechanism is disposed in the head.

13. The intramedullary rod of claim 11 wherein the mechanism includes a control element in the head and accessible at the proximal end for causing the mechanism to pivot the fastener in situ.

14. An intramedullary rod for use with a fastener to repair a bone in a mammalian body comprising an elongate nail extending along a longitudinal axis and having a stem and a head, the head being provided with an aperture extending at an angle to the longitudinal axis and adapted to receive the fastener, and a sleeve carried by the head and slidable longitudinally relative to the head to engage the fastener so as to pivot the fastener in situ from a first angled position relative to the head to a second angled position relative to the head.

15. The intramedullary rod of claim 14 wherein the head includes a proximal end, further comprising a control element carried by the head and coupled to the sleeve, the control element being accessible at the proximal end for moving the sleeve longitudinally relative to the head so as to pivot the fastener.

16. The intramedullary rod of claim 14 wherein sleeve is provided with an opening for receiving the fastener.

17. The intramedullary rod of claim 14 wherein the sleeve has a cross-sectional configuration that is substantially C shaped.

18. The intramedullary rod of claim 14 wherein the head is provided with first and second openings for forming at least part of the aperture, the movement of the sleeve pivoting the fastener about the first opening.

19. An intramedullary rod for use with a fastener to repair a bone in a mammalian body comprising an elongate nail extending along a longitudinal axis and having a stem and a head, the head having a proximal end and being provided with a recess extending along the longitudinal axis from an opening on the longitudinal axis and having first and second additional openings communicating with the recess fir forming an aperture through the head extending at an angle to the longitudinal axis and adapted to receive the fastener, a sleeve disposed in the recess of the head in the vicinity of the second opening and slidable along the longitudinal axis and a control element disposed in the head and coupled to the sleeve, the control element being accessible through the opening at the proximal end for moving the sleeve longitudinally relative to the head so as to pivot the fastener in situ about the first opening from a first angled position relative to the head to a second angled position relative to the head.

20. The intramedullary rod of claim 19 wherein sleeve is provided with an opening for receiving the fastener.

21. The intramedullary rod of claim 19 wherein the sleeve has a cross-sectional configuration that, is substantially C shaped.

22. An intramedullary rod for use with a fastener to repair a bone in a mammalian body comprising an elongate nail extending along a longitudinal axis and having a stem and a head, the head having a proximal end and being provided with a recess and first and second openings communicating with the recess for forming an aperture through the head extending at an angle to the longitudinal axis and adapted to receive the fastener, a sleeve provided with an opening for receiving the fastener disposed in the recess of the head and slidable along the longitudinal axis and a threaded control element disposed in the head and coupled to the sleeve, the threaded control element being accessible at the proximal end for moving the sleeve longitudinally in the head so as to engage the fastener.

23. The intramedullary rod of claim 22 wherein the sleeve has a cross-sectional configuration that is substantially C shaped.

24. The intramedullary rod of claim 22 wherein the sleeve is configured to limit pivoting of the fastener about an axis.

25. An intramedullary rod for use with a fastener having an outer cylindrical surface provided with a plurality of longitudinally-extending slots in the surface to repair a bone in a mammalian body comprising an elongate nail extending along a longitudinal axis and having a stem and a head, the head having a proximal end and being provided with a recess and first and second openings communicating with the recess for forming an aperture through the head extending at an angle to the longitudinal axis and adapted to receive the fastener, a sleeve disposed in the recess of the head and slidable along the longitudinal axis and being provided with a transverse opening for receiving the fastener, and a set screw at least partially disposed in the sleeve and being accessible at the proximal end for extending along the sleeve into one of the plurality of longitudinally-extending slots in the fastener for rotatably locking the fastener relative to the head.

26. The intramedullary rod of claim 25 wherein the sleeve has a cross-sectional configuration that is substantially C shaped.

* * * * *